United States Patent [19]
Muller et al.

[11] Patent Number: 6,130,226
[45] Date of Patent: Oct. 10, 2000

[54] IMMUNOTHERAPEUTIC AGENTS

[75] Inventors: George W. Muller, Bridgewater; Mary Shire, North Plainfield, both of N.J.

[73] Assignee: Celgene Corporation, Warren, N.J.

[21] Appl. No.: 09/271,683

[22] Filed: Mar. 18, 1999

Related U.S. Application Data

[60] Division of application No. 08/909,201, Aug. 11, 1997, Pat. No. 5,929,117, which is a continuation-in-part of application No. 08/695,599, Aug. 12, 1996, abandoned.

[51] Int. Cl.$^7$ .................. A61K 31/345; A61K 31/44; A61P 11/06; C07D 211/80

[52] U.S. Cl. .................. 514/277; 514/344; 514/345; 514/346; 514/349; 514/350; 514/351; 514/352; 514/354; 546/249; 546/348; 546/286; 546/288; 546/289; 546/290; 546/291; 546/292; 546/304; 546/314; 546/329; 546/345

[58] Field of Search .................. 514/277; 546/349, 546/348

[56] References Cited

U.S. PATENT DOCUMENTS 5,135,940  8/1992  Belanger et al. .................. 514/381

FOREIGN PATENT DOCUMENTS

| | | |
|---|---|---|
| 0395446 | 10/1990 | European Pat. Off. . |
| 3525623 | 1/1987 | Germany . |
| 4220983 | 1/1994 | Germany . |
| 44-026659 | 7/1969 | Japan . |
| 94/14742 | 7/1994 | WIPO . |
| 94/14800 | 7/1994 | WIPO . |
| 94/20455 | 9/1994 | WIPO . |
| 96/20926 | 7/1996 | WIPO . |
| 96/21435 | 7/1996 | WIPO . |

OTHER PUBLICATIONS

R. W. Guthrie, et. Al., "Pentadienyl Carboxamide Derivatives as Antagonists of Platelet–Activating Factor", *Journal of Medicinal Chemistry*, vol. 32, No. 8, pp. 1820–1835 (1989). Chem. SQ 8924.503.

Abe S. et al. "beta–Acrylcinnamitriles", Chemical Abstracts, vol. 72(5), 1970 Abstract. 21510t.

Erickson, M. et al. "Gaschroatographische Analye von Liginoxydationsprodukten. VII. Ein verbessertes Verfahren zur Charakterierung von Ligninen durch Methylierung und oxydativen Abbau" *ACTA Chemica Scandinavica*, vol. 27(1), 1973, pp. 127–140 compounds 40–46 p. 134.

Zarubin M.Y. et al., "Acid–base reactions to lignin with strong acids", Chemical Abstracts, vol. 83(14), 1975, Abs. Khin & Dev. vol. 3, 1975 117388n.

Mamadzhanov A. et al., Condensation of pyrocatechol and its methyl ethers with alpha–phenylbenzyl alcohols in the presence of polyphosphoric acid:, Chemical Abstracts, vol. 94(25), 1981 208463b.

*Primary Examiner*—Joseph McKane
*Assistant Examiner*—Jane C. Oswecki
*Attorney, Agent, or Firm*—Mathews, Collins, Shepherd & Gould, P.A.

[57] ABSTRACT

Cyano and carboxy derivatives of substituted styrenes are inhibitors of tumor necrosis factor α, nuclear factor κB, and phosphodiesterase and can be used to combat cachexia, endotoxic shock, retrovirus replication, asthma, and inflammatory conditions. A typical embodiment is 3,3-bis-(3,4-dimethoxyphenyl)acrylonitrile.

10 Claims, No Drawings

IMMUNOTHERAPEUTIC AGENTS

CROSS-REFERENCE TO RELATED APPLICATIONS

This is a divisional of Ser. No. 08/909,201 filed Aug. 11, 1997, now U.S. Pat. No. 5,929,117, which is a continuation-in-part of Ser. No. 08/695,599 filed Aug. 12, 1996, abandoned.

BACKGROUND OF THE INVENTION

This invention relates to a method of reducing the level of cytokines and their precursors in mammals and to compounds and compositions useful therein. In particular, the invention pertains to a class of compounds which mediate the action of phosphodiesterases, particularly PDE III and PDE IV, and the formation of TNFα and NFκB.

Tumor necrosis factor alpha, (INFα) is a cytokine which is released primarily by mono-nuclear phagocytes in response to immunostimulators. When administered to animals or humans, TNFα can cause inflammation, fever, cardiovascular effects, hemorrhage, coagulation, and acute phase responses similar to those seen during acute infections and shock states.

The nuclear factor κB (NFκB) is a pleiotropic transcriptional activator (Lenardo, et al., Cell 1989, 58, 227–29) which has been implicated in a variety of disease and inflammatory states. NFκB is thought to regulate cytokine levels including, but not limited to, TNFα and to be an activator of HIV transcription (Dbaibo et al., J. Biol. Chem. 1993, 17762–66; Duh et al., Proc. Natl. Acad. Sci. 1989, 86, 5974–78; Bachelerie et al., Nature 1991, 350, 709–12; Boswas et al., J. Acquired Immune Deficiency Syndrome 1993, 6, 778–786; Suzuki et al., Biochem. And Biophys. Res. Comm. 1993, 193, 277–83; Suzuki et al., Biochem. And Biophys. Res. Comm. 1992, 189, 1709–15; Suzuki et al., Biochem. Mol. Bio. Int. 1993, 31(4), 693–700; Shakhov et al. 1990, 171, 35–47; and Staal et al., Proc. Natl. Acad. Sci. USA 1990, 87, 9943–47). Thus, inhibition of NFκB binding can regulate transcription of cytokine gene(s) and through this modulation and other mechanisms be useful in the inhibition of a multitude of disease states. TNFα and NFκB levels are influenced by a reciprocal feedback loop.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, Drugs of the Future, 17(9), 799–807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle. The primary cellular mechanism for the inactivation of cAMP is the break-down of cAMP by a family of isoenzymes referred to as cyclic nucleotide phosphodiesterases (PDE), of which seven are known. It is recognized, for example, that the inhibition of PDE type IV is particularly effective in both the inhibition of inflammatory mediator release and the relaxation of airway smooth muscle. Thus, compounds which inhibit PDE IV exhibit the desirable inhibition of inflammation and relaxation of airway smooth muscle with a minimum of unwanted side effects, such as cardiovascular or anti-platelet effects. It is now known that inhibition of TNFα production is a consequence of inhibition of PDE IV. L. J. Lombardo, Current Pharmaceutical design, 1, 255–268 (1995).

Excessive or unregulated TNFα production has been implicated in a number of disease conditions. These include endotoxemia and/or toxic shock syndrome {Tracey et al., Nature 330, 662–664 (1987) and Hinshaw et al., Circ. Shock 30, 279–292 (1990)}; cachexia {Dezube et al., Lancet, 335 (8690), 662 (1990)}; and Adult Respiratory Distress Syndrome (ARDS) where TNFα concentrations in excess of 12,000 pg/milliliters have been detected in pulmonary aspirates from ARDS patients {Millar et al., Lancet 2 (8665), 712–714 (1989)}. Systemic infusion of recombinant TNFα also resulted in changes typically seen in ARDS {Ferrai-Baliviera et al., Arch. Surg. 124(12), 1400–1405 (1989)}.

TNFα also appears to be involved in bone resorption diseases, including arthritis where it has been determined that when activated, leukocytes will produce a bone-resorbing activity, and data suggests that TNFα contributes to this activity {Bertolini et al., Nature 319, 516–518 (1986) and Johnson et al., Endocrinology 124(3), 1424–1427 (1989)}. It has been determined that TNFα stimulates bone resorption and inhibits bone formation in vitro and in vivo through stimulation of osteoblast formation and activation in combination with inhibition of osteoblast function. Although TNFα may be involved in many bone resorption diseases, including arthritis, the most compelling link with disease is the association between production of TNFα by tumor or host tissues and malignancy associated hypercalcemia {Calci. Tissue Int. (US) 46 (Suppl.), S3-10 (1990)}. In Graft versus Host Reaction, increased serum TNFα levels have been associated with major complications following acute allogenic bone marrow transplants {Holler et al., Blood, 75(4), 1011–1016 (1990)}.

Cerebral malaria is a lethal hyperacute neurological syndrome associated with high blood levels of TNFα and is the most severe complication occurring in malaria patients. Levels of serum TNFα correlated directly with the severity of the disease and the prognosis in patients with acute malaria attacks {Grau et al., N. Engl. J. Med. 320 (24), 1586–1591 (1989)}.

Macrophage-induced angiogenesis is known to be mediated by TNFα. Leibovich et al. {Nature, 329, 630–632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth. TNFα production also has been associated with cancerous conditions, particularly induced tumors {Ching et al., Brit. J. Cancer, (1955) 72, 339–343, and Koch, Progress in Medicinal Chemistry, 22, 166–242 (1985)}.

TNFα also appears to play a role in the area of chronic pulmonary inflammatory diseases. The deposition of silica particles leads to silicosis, a disease of progressive respiratory failure caused by a fibrotic reaction. Antibodies to TNFα completely blocked the silica-induced lung fibrosis in mice {Pignet et al., Nature, 344:245–247 (1990)}. High levels of TNFα production (in the serum and in isolated macrophages) have been demonstrated in animal models of silica and asbestos induced fibrosis {Bissonnette et al., Inflammation 13(3), 329–339 (1989)}. Alveolar macrophages from pulmonary sarcoidosis patients have also been found to spontaneously release massive quantities of TNFα as compared with macrophages from normal donors {Baughman et al., J. Lab. Clin. Med. 115 (1), 36–42 (1990)}.

TNFα is also implicated in the inflammatory response which follows reperfusion, called reperfusion injury, and is a major cause of tissue damage after loss of blood flow {Vedder et al., PNAS 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., *J. Cell Biol.* 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., *Am. J. Path.* 135 (1), 121–132 (1989)}.

TNFα blockage with monoclonal anti-TNFα antibodies has been shown to be beneficial in rheumatoid arthritis {Elliot et al., *Int. J. Pharmac.* 1995 17(2), 141–145}. High levels of TNFα are associated with Crohn's disease {von Dullemen et al., *Gastroenterology*, 1995 109(1), 129–135} and clinical benefit has been achieved with TNFα antibody treatment, thus confirming the importance of TNFα in the disease.

Moreover, it is now known that TNFα is a potent activator of retrovirus replication including activation of HIV-1. {Duh et al., *Proc. Nat. Acad. Sci.* 86, 5974–5978 (1989); Poll et al., *Proc. Nat. Acad. Sci.* 87, 782–785 (1990); Monto et al., *Blood* 79, 2670 (1990); Clouse et al., *J. Immunol.* 142, 431–438 (1989); Poll et al., *AIDS Res. Hum. Retrovirus*, 191–197 (1992)}. AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1 and HIV-2, infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in a HIV-infected individual aids in limiting the maintenance of T lymphocyte activation caused by HIV infection.

Monocytes, macrophages, and related cells, such as kupffer and glial cells, have also been implicated in maintenance of the HIV infection. These cells, like T cells, are targets for viral replication and the level of viral replication is dependent upon the activation state of the cells {Rosenberg et al., *The Immunopathogenesis of HIV Infection*, Advances in Immunology, 57 (1989)}. Cytokines, such as TNFα, have been shown to activate HIV replication in monocytes and/or macrophages {Poli et al. *Proc. Natl. Acad. Sci.*, 87, 782–784 (1990)}, therefore, prevention or inhibition of cytokine production or activity aids in limiting HIV progression as stated above for T cells. Additional studies have identified TNFα as a common factor in the activation of HIV in vitro and has provided a clear mechanism of action via a nuclear regulatory protein found in the cytoplasm of cells (Osbom, et al., *PNAS* 86, 2336–2340). This evidence suggests that a reduction of TNFα synthesis may have an antiviral effect in HIV infections, by reducing the taanscription and thus virus production.

AIDS viral replication of latent HIV in T cell and macrophage lines can be induced by TNFα {Folks et al., *PNAS* 86, 2365–2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., *PNAS* 86, 2336–2340 (1989)}. TNFα in AIDS associated cachexia is suggested by elevated serum TNFα and high levels of spontaneous TNFα production in peripheral blood monocytes from patients {Wright et al., *J. Immunol.* 141 (1), 99–104 (1988)}.

TNFα has been implicated in other viral infections, such as the cytomegalia virus (CMV), influenza virus, adenovirus, and the herpes family of viruses for similar reasons as those noted.

It is recognized that suppression of the effects of TNFα can be beneficial in a variety of conditions and in the past, steroids such as dexamethasone and prednisone as well as polyclonal and monoclonal antibodies {Beutler et al., *Science* 234, 470–474 (1985); WO 92/11383} have been employed for this purpose. Conditions in which the inhibition of TNFα is desirable include septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis and other arthritic conditions, Crohn's disease, ulcerative colitis, multiple sclerosis, systemic lupus erythrematosis, ENL in leprosy, radiation damage, asthma, and hyperoxic alveolar injury.

The suppression of the action of NFκB in the nucleus can be useful in the treatment of a variety of diseases including but not limited to rheumatoid arthritis, rheumatoid spondylitis, osteoarthritis, other arthritic conditions, septic shock, septis, endotoxic shock, graft versus host disease, wasting, Crohn's disease, ulcerative colitis, multiple sclerosis, systemic lupus erythrematosis, ENL in leprosy, HIV, AIDS, and opportunistic infections in AIDS.

DETAILED DESCRIPTION

The compounds of the present invention affect the levels of phosphodiesterases, TNFα and NFκB and the method involves the regulation of the levels of phosphodiesterases, TNFα and NFκB through the administration of compounds of the formula:

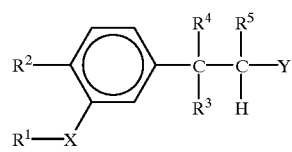

I in which:

(a) X is —O— or —$(C_nH_{2n})$— in which n has a value of 0, 1, 2, or 3, and $R^1$ is alkyl of one to 10 carbon atoms, monocycloalkyl of up to 10 carbon atoms, polycycloalkyl of up to 10 carbon atoms, or benzocyclic alkyl of up to 10 carbon atoms, or (b) X is —CH= and R$^1$ is alkylidene of up to 10 carbon atoms, monocycloalkylidene of up to 10 carbon atoms, or bicycloalkylidene of up to 10 carbon atoms;

R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;

R$^3$ is (i) phenyl, unsubstituted or substituted with 1 or more substituents each selected independently from nitro, cyano, halo, trifluoromethyl, carbethoxy, carbomethoxy, carbopropoxy, acetyl, carbarnoyl, carbamoyl substituted with alkyl of 1 to 3 carbon atoms, acetoxy, carboxy, hydroxy, amino, amino substituted with an alkyl of 1 to 5 carbon atoms, alkyl of up to 10 carbon atoms, cycloalkyl of up to 10 carbon atoms, alkoxy of up to 10 carbon atoms, cycloalkoxy of up to 10 carbon atoms, alkylidenemethyl of up to 10 carbon atoms, cycloalkylidenemethyl of up to 10 carbon atoms, phenyl, or methylenedioxy; (ii) pyridine, substituted pyridine, pyrrolidine, imidizole, naphthalene, or thiophene; (iii) cycloalkyl of 4–10 carbon atoms, unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl;

each of R$^4$ and R$^5$ taken individually is hydrogen or R$^4$ and R$^5$ taken together are a carbon-carbon bond;

Y is —COZ, —C≡N, or lower alkyl of 1 to 5 carbon atoms;

Z is —OH, —NR$^6$R$^6$, —R$^7$, or —OR$^7$;

R$^6$ is hydrogen or lower alkyl; and

R$^7$ is alkyl or benzyl.

One preferred group are the compounds of Formula I in which R$^1$ is alkyl, monocycloalkyl of up to 10 carbon atoms, polycycloalkyl of up to 10 carbon atoms, or benzocyclic alkyl of up to 10 carbon atoms; X is —(CH$_2$)$_n$— or —O—, where n=0, 1, 2, or 3; R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkoxy, halo; and R$^4$, R$^5$, Y, Z, R$^6$, and R$^1$ are as therein defined.

A second preferred group of compounds are those of Formula I in which R$^3$ is (i) phenyl or naphthalene, unsubstituted or substituted with 1 or more substituents each selected independently from nitro, cyano, halo, trifluoromethyl, carbethoxy, carbomethoxy, carbopropoxy, acetyl, carbamoyl, or carbamoyl substituted with alkyl of 1 to 3 carbon atoms, acetoxy, carboxy, hydroxy, amino, amino substituted with an alkyl of 1 to 5 carbon atoms, alkyl or cycloalkyl of 1 to 10 carbon atoms, alkoxy or cycloalkoxy of 1 to 10 carbon atoms; or (ii) cycloalkyl of 4 to 10 carbon atoms, unsubstituted or substituted with one or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or phenyl.

Particularly preferred nitriles are compound of the formula:

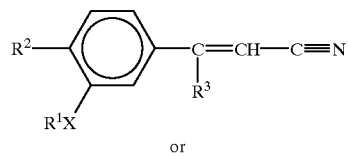

IIA

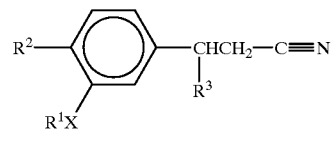

IIB wherein:
(a) X is —O— or —(C$_n$H$_{2n}$)— in which n has a value of 0, 1, 2, or 3, and R$^1$ is alkyl of up to 10 carbon atoms, monocycloalkyl of up to 10 carbon atoms, polycycloalkyl of up to 10 carbon atoms, or benzocyclic alkyl of up to 10 carbon atoms, or (b) X is —CH=, and R$^1$ is alkylidene of up to 10 carbon atoms or monocycloalkylidene of up to 10 carbon atoms;

R$^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkoxy, or halo; and R$^3$ is (i) phenyl or naphthyl, unsubstituted or substituted with 1 or more substituents each selected independently from nitro, cyano, halo, trifluoromethyl, carbethoxy, carbomethoxy, carbopropoxy, acetyl, carbamoyl, or carbamoyl substituted with alkyl of 1 to 3 carbon atoms, acetoxy, carboxy, hydroxy, amino, amino substituted with an alkyl of 1 to 5 carbon atoms, alkoxy or cycloalkoxy of 1 to 10 carbon atoms; or (ii) cycloalkyl of 4 to 10 carbon atoms, unsubstituted or substituted with one or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or phenyl.

Particularly preferred alkanoic acid derivatives are compound of the formula:

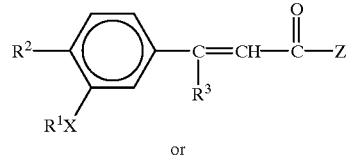

IIIA

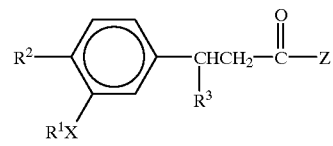

IIIB wherein:
(a) X is —O— or —(C$_n$H$_{2n}$)— in which n has a value of 0, 1, 2, or 3, and R$^1$ is alkyl of up to 10 carbon atoms, monocycloalkyl of up to 10 carbon atoms, polycycloalkyl of up to 10 carbon atoms, or benzocyclic alkyl of up to 10 carbon atoms, or (b) X is —CH=, and R¹ is alkylidene of up to 10 carbon atoms or monocycloalkylidene of up to 10 carbon atoms;

R² is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkoxy, or halo;

R³ is (i) phenyl or naphthyl, unsubstituted or substituted with one or more substituents each selected independently from nitro, cyano, halo, trifluoromethyl, carbethoxy, carbomethoxy, carbopropoxy, acetyl, carbamoyl, or carbamoyl substituted with alkyl of 1 to 3 carbon atoms, acetoxy, carboxy, hydroxy, amino, amino substituted with an alkyl of 1 to 5 carbon atoms, alkyl or cycloalkyl of 1 to 10 carbon atoms, alkoxy or cycloalkoxy of 1 to 10 carbon atoms; or (ii) cycloalkyl of 4 to 10 carbon atoms, unsubstituted or substituted with one or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or phenyl; and Z is —OH, —NR⁶R⁶, R⁷, or —OR⁷ in which R⁶ is hydrogen or lower alkyl; and R⁷ is alkyl or benzyl.

The term alkyl as used herein denotes a univalent saturated branched or straight hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified by "lower", the alkyl group will contain from 1 to 6 carbon atoms. The same carbon content applies to the parent term "alkane" and to derivative terms such as "alkoxy".

The term cycloalkyl as used herein denotes a univalent saturated cyclic hydrocarbon chain. Unless otherwise stated, such chains can contain up to 18 carbon atoms. Monocyclicalkyl refers to groups having a single ring group. Polycycloalkyl denotes hydrocarbon systems containing two or more ring systems with two or more ring carbon atoms in common. Benzocycloalkyl signifies a monocyclicalkyl group fused to a benzo group. Representative of monocycloalkyl groups are cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, and cyclooctadecyl. Representative of polycycloalkyl include bicyclo[2.2.1]heptyl, bicyclo[3.2.1] octyl, and bicyclo[2.2.2]octyl. Benzocycloalkyl is typified by tetrahydronaphthyl, indanyl, and 1.2-benzocycloheptanyl.

The compounds can be prepared using methods which are known in general for the preparation of diaryl alkenes. For example, an appropriately substituted bis(aryl) ketone can be treated with a dialkyl cyanomethylphosphonate to yield the corresponding bis aryl acrylonitrile. This can be hydrolysed to the corresponding carboxylic acid, esters and amides by methods known per se. Alternatively, the substituted bis(aryl) ketone can be treated with an alkyl disubstituted phosphonoacetate or a disubstituted carbamoylmethylphosphonate and lithium hexamethyldisilazide to form the ester or amide, respectively, directly. The substituted bis(aryl) ketone alternatively can be treated with the appropriate triphenylphosphite.

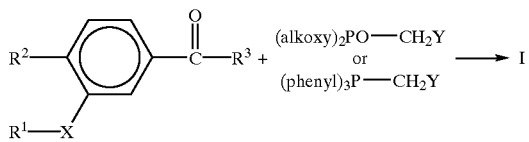

The bis(aryl) ketones also are obtained by methods known per se such as for example by Friedel-Crafts acylations with acid chlorides in the presence of a Lewis acid.

Representative examples of these compounds include 3,3-bis-(3,4-dimethoxyphenyl)-acrylonitrile, 3,3-bis-(3-ethoxy-4-methoxyphenyl)acrylonitrile, methyl 3,3-bis-(3-ethoxy-4-methoxyphenyl)-propenoate, methyl 3-(3-ethoxy-4-methoxyphenyl)-3-phenylpropenoate, 3-(3-propoxy-4-methoxyphenyl)-3-phenylacrylonitrile, 3-(3-ethoxy-4-methoxyphenyl)-3-phenylacrylonitrile, 3,3-bis-(3-cyclopentoxy-4-methoxyphenyl)acrylonitrile, methyl 3-(3-cyclopentoxy-4-methoxyphenyl)-3-phenylpropenoate, 3-(3-cyclopentoxy-4-methoxyphenyl)-3-phenylacrylonitrile, 3-(3-cyclopentoxy-4-methoxyphenyl)-3-phenylpropene, 1-(3-cyclopentoxy-4-methoxyphenyl)-1-phenylpropane, 3-(3-cyclopentoxy-4-methoxyphenyl)-3-phenylpropanenitrile, methyl 3-(3-cyclopentoxy-4-methoxyphenyl)-3-phenylpropanoate, 3-(3-ethoxy-4-methoxyphenyl)-3-phenylpropanenitrile, methyl 3-(3-ethoxy-4-methoxyphenyl)-3-phenylpropanoate, 3,3-bis-(3,4-dimethoxyphenyl)propanenitrile, 3,3-bis-(3-ethoxy-4-methoxyphenyl)propanenitrile, 3-(3,4-dimethoxyphenyl)-3-phenylacrylonitrile, 3-(3-ethoxy-4-methoxyphenyl)-3-naphthylpropanenitrile, 3-(3,4-dimethoxyphenyl)-3-phenylpropanenitrile, and 3-(3,4-dimethoxyphenyl)-3-(3-ethoxy-4-methoxyphenyl)propanenitrile.

A further group of preferred compounds include 4,4-bis-(3,4-dimethoxyphenyl)but-3-en-2-one; 4-(3,4-dimethoxyphenyl)-4-(3-ethoxy-4-methoxyphenyl)but-3-en-2-one; 4-(3,4-dimethoxyphenyl)-4-phenylbut-3-en-2-one; 4-(3,4-dimethoxyphenyl)-4-(3-cyclopentoxy-4-methoxyphenyl)but-3-en-2-one; 4-(3,4-dimethoxyphenyl)-4-(3-indan2-yloxy-4-methoxyphenyl)but-3-en-2-one; 4-(3-ethoxy-4-methoxyphenyl)-4-(4-pyridyl)but-3-en-2-one; 4-(3-ethoxy-4-methoxyphenyl)-4-(4-pyridyl)butan-2-one; 4-(3-cyclopentoxy-4-methoxyphenyl)-4-(4-pyridyl)but-3-en-2-one; 4-(3-cyclopentoxy-4-methoxyphenyl)-4-(4-pyridyl)butan-2-one; methyl 3-(3-cyclopentoxy-4-methoxyphenyl)-3-(4-pyridyl)prop-2-enoate; methyl 3-(3-ethoxy-4-methoxyphenyl)-3-(4-pyridyl)prop-2-enoate; methyl 3-(3-ethoxy-4-methoxyphenyl)-3-(4-pyridyl) propanoate; 4-(3-ethoxy-4-methoxyphenyl)-4-(2-furyl)but-3-en-2-one; 3-(3-ethoxy-4-methoxyphenyl)-3-(2-furyl)prop-2-enenitrile; 3-(3-ethoxy-4-methoxyphenyl)-3-(4-pyridyl)prop-2-enenitrile; 3-(3-ethoxy-4-methoxyphenyl)-3-(4-pyridyl)propanenitrile; 3-(3-cyclopentoxy-4-methoxyphenyl)-3-(4-pyridyl)prop-2-enenitrile; 3-(3-cyclopentoxy-4-methoxyphenyl)-3-(4-pyridyl) propanenitrile; 4-(3,4-dimethoxyphenyl)-4-(4-methoxy-3-prop-1-enylphenyl)but-3-en-2-one; 4-(3,4-dimethoxyphenyl)-4-(4-methoxy-3-prop-1-enylphenyl)but-3-en-2-one; 4,4-bis-(3,4-dimethoxyphenyl)butan-2-one; 4-(3,4-dimethoxyphenyl)-4-(3-ethoxy-4-methoxyphenyl)butan-2-one; 4-(3,4-dimethoxyphenyl)-4-(3-(cyclopentylidenemethyl)-4-methoxyphenyl)butan-2-one; 4-(3,4-dimethoxyphenyl)-4-(4-methoxy-3-prop-1- enylphenyl)butan-2-one; 4,4-bis-(3-ethoxy-4-methoxyphenyl)but-3-en-2-one; 3-(3,4-dimethoxyphenyl)-3-(3-(cyclopentylidenemethyl)-4-methoxyphenyl)prop-2-enenitrile; 3-(3-(cyclopentylidenemethyl)-4-methoxyphenyl)-3-phenyl-prop-2-enenitrile; 1-(3,4-dimethoxyphenyl)-1-(3-ethoxy-4-methoxyphenyl)pentan-3-one; 1-(3,4-dimethoxyphenyl)-1 -(3-ethoxy-4-methoxyphenyl)pent-1-en-3-one; 1,1-bis-(3,4-dimethoxyphenyl)pentan-3-one; 3-(3,4-dimethoxyphenyl)-3-(3-(cyclopentylidenemethyl)-4-methoxyphenyl)prop-2-enenitrile; 3-(3-(cyclopentylidenemethyl)-4-methoxyphenyl)-3-phenyl-propanenitrile; 3,3-bis-(3-(cyclopentylidenemethyl)-4-methoxyphenyl)propanenitrile; 3,3-bis-(3-(cyclopentylidenemethyl)-4-methoxyphenyl)prop-2-enenitrile; 3-(3,4-dimethoxyphenyl)-3-(3-(cyclopentylidenemethyl)-4-methoxyphenyl)prop-2-enamide; 3-(3-(cyclopentylidenemethyl)-4-methoxyphenyl-3-phenyl)propanamide; 3,3-bis-(3-(cyclopentylidenemethyl)-4-methoxyphenyl)propanamide; 3,3-bis-(3-(cyclopentylidenemethyl)-4-methoxyphenyl)prop-2-enamide; 3-(3,4-dimethoxyphenyl)-3-(3-ethoxy-4-methoxyphenyl)prop-2-enamide; 3,3-bis-(3-ethoxy-4-methoxyphenyl)prop-2-enamide; 3,3-bis-(3,4-dimethoxyphenyl)prop-2-enamide; 3,3-bis-(3-ethoxy-4-methoxyphenyl)propanamide; 3,3-bis-(3,4-dimethoxyphenyl)propanamide; 4-(3,4-dimethoxyphenyl)-4-(4-methoxy-3-exo-norbornyloxyphenyl)but-3-en-2-one; 3-(3,4-dimethoxyphenyl)-3-(4-methoxy-3-exo-norbornyloxyphenyl)prop-2-enenitrile; 3-(3,4-dimethoxyphenyl)-3-(3,4-methylenedioxyphenyl)prop-2-enenitrile; 3-(4-aminophenyl)-3-(3,4-dimethoxyphenyl)prop-2-enenitrile; and 3-(4-aminophenyl)-3-(3-ethoxy-4-dimethoxyphenyl)prop-2-enenitrile.

These compounds may possess one or more centers of chirality and thus can exist as optical isomers. Both the racemates of these isomers and the individual isomers themselves, as well as diastereoisomers when there are two or more chiral centers, are within the scope of the present invention. The racemates can be used as such or can be separated into their individual isomers mechanically as by chromatography using a chiral absorbent. Alternatively, the individual isomers can be prepared in chiral form or separated chemically from a mixture by forming salts with a chiral acid, such as the individual enantiomers of 10-camphorsulfonic acid, camphoric acid, alpha-bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as to obtain either or both isomers substantially free of the other; i.e., in a form having an optical purity of >95%. In addition, the compounds in which $R^4$ and $R^5$ taken together are a carbon-carbon bond can exist as cis (Z) and trans (E) isomers.

The compounds can be used, under the supervision of qualified professionals, to inhibit the undesirable effects of TNFα, NFκB, and phosphodiesterase. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20–100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 1 to about 1000 milligrams/day as needed in single or multiple daily administration. In general, an initial treatment regimen can be copied from that known to be effective in interfering with TNFα activity for other TNFα mediated disease states by the compounds of the present invention. Treated individuals will be regularly checked for T cell numbers and T4/T8 ratios and/or measures of viremia such as levels of reverse transcriptase or viral proteins, and/or for progression of cytokine-mediated disease associated problems such as cachexia or muscle degeneration. If no effect is observed following the normal treatment regimen, then the amount of cytokine activity interfering agent administered is increased, e.g., by fifty percent a week.

The compounds of the present invention can also be used topically in the treatment or prophylaxis of topical disease states mediated or exacerbated by excessive TNFα production, such as viral infections, for example those caused by the herpes viruses or viral conjunctivitis, psoriasis, other skin disorders and diseases, etc.

The compounds can also be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

Inhibition of PDE III, PDE IV, TNFα and NFκB by these compounds can be conveniently assayed using methods known in the art, e.g., enzyme immunoassay, radioimmunoassay, immunoelectrophoresis, affinity labeling, etc., of which the following are typical.

Enzyme-linked Immunosorbent Assay for TNFα

PBMC isolation: PBMC from normal donors were obtained by Ficoll-Hypaque density centrifugation. Cells were cultured in RPMI supplemented with 10% AB+ serum, 2 mM L-glutamine, 100 U/mL penicillin and 100 mg/mL streptomycin.

PBMC suspensions: Drugs. were dissolved in dimethylsulfoxide (Sigma Chemical), further dilutions were done in supplemented RPMI. The final dimethylsulfoxide concentration in the presence or absence of drug in the PBMC suspensions was 0.25 wt %. Drugs were assayed at half-log dilutions starting at 50 mg/mL. Drugs were added to PBMC ($10^6$ cells/mL) in 96 wells plates one hour before the addition of LPS.

Cell stimulation: PBMC ($10^6$ cells/mL) in the presence or absence of drug were stimulated by treatment with 1 mg/mL of LPS from *Salmonella Minnesota* R595 (List Biological Labs, Campbell, Calif.). Cells were then incubated at 37° C. for 18–20 hours. Supernatants were then harvested and assayed immediately for TNFα levels or kept frozen at −70° C. (for not more than 4 days) until assayed.

TNFα Determination: The concentration of TNFα in the supernatant was determined by human TNFα ELISA kits (ENDOGEN, Boston, Mass.) according to the manufacturer's directions.

Phosphodiesterase can be determined in conventional models. For example, using the method of Hill and Mitchell, U937 cells of the human promonocytic cell line are grown to $1 \times 10^6$ cells/mL and collected by centrifugation. A cell pellet of $1 \times 10^6$ cells is washed in phosphate buffered saline and then frozen at $-70°$ C. for later purification or immediately lysed in cold homogenization buffer (20 mM Tris-HCl, pH 7.1, 3 mM 2-mercaptoethanol, 1 mM magnesium chloride, 0.1 mM ethylene glycol-bis-(β-aminoethyl ether)-N,N,N',N'-tetraacetic acid (EGTA), 1 μM phenylmethylsulfonyl fluoride (PMSF), and 1 μg/mL leupeptin). Cells are homogenized with 20 strokes in a Dounce homogenizer and supernatant containing the cytosolic fraction are obtained by centrifugation. The supernatant then is loaded onto a Sephacryl S-200 column equilibrated in homogenization buffer. Phosphodiesterase is eluted in homogenization buffer at a rate of approximately 0.5 mL/min and fractions are assayed for phosphodiesterase activity-/+rolipram. Fractions containing phosphodiesterase activity (rolipram sensitive) are pooled and aliquoted for later use.

The phosphodiesterase assay is carried out based on procedure described by Hill and Mitchell. The assay is carried out in a total volume of 100 μl containing various concentration of test compounds, 50 mM Tris-HCl, pH 7.5,5 mM magnesium chloride and 1 μM cAMP of which 1% was $^3$H cAMP. Reactions are incubated at 30° C. for 30 minutes and terminated by boiling for 2 minutes. The amount of phosphodiesterase IV containing extract used for these experiments is predetermined such that reactions are within the linear range and consumed less than 15% of the total substrate. Following termination of reaction, samples are chilled at 4° C. and then treated with 10 μl 10 mg/mL snake venom for 15 min at 30° C. Unused substrate then is removed by adding 200 μl of a quaternary ammonium ion exchange resin (AG1-X8, BioRad) for 15 minutes. Samples then are spun at 3000 rpm, 5 min and 50 μl of the aqueous phase are taken for counting. Each data point is carried out in duplicate and activity is expressed as percentage of control. The $IC_{50}$ of the compound then is determined from dose response curves of a minimum of three independent experiments.

The following examples will serve to further typify the nature of this invention but should not be construed as a limitation in the scope thereof, which scope is defined solely by the appended claims.

EXAMPLE 1

3,3-bis-(3,4-Dimethoxyphenyl)acrylonitrile

A. 3,4,3',4,'-Tetramethoxybenzophenone

To a stirred ice bath cooled solution of veratole (2.07 g, 15.0 mmol) in 30 mL of methylene chloride under nitrogen was added aluminum chloride (2.20 g, 16.5 mmol). A slight exotherm resulted. To the reaction mixture was then added 3,4-dimethoxybenzoyl chloride (3.01 g, 15.0 mmol) and 20 mL of methylene chloride. The reaction was then allowed to warm to room temperature and then refluxed for 3.5 hours and then allowed to stir at room temperature for 16 hours. The reaction mixture was then poured into 50 mL of ice water and stirred for 15 minutes. This mixture was extracted with methylene chloride (2×25 mL each). The combined extracts were dried over sodium sulfate and concentrated in vacuo to afford the crude product as a tan solid. The crude product was purified by flash chromatography (silica gel, 4/96 ethyl acetate/methylene chloride) to afford 2.97 g (66%) of the product as a white powder: $^1$H NMR (CDCl$_3$) δ 7.4 (m, 4 H), 6.91 (m, 2 H), 3.97 (s, 6 H), 3.95 (s, 6 H); $^{13}$C NMR (DMSO-d$_6$) δ 194.4, 152.5, 148.8, 130.7, 124.7, 112.2, 109.7, 56.0. Anal. Calcd for $C_{17}H_{18}O_5$. Theoretical: C, 67.54; H, 6.00. Found: C, 67.42; H, 6.03.

B. 3,3-bis-(3',4'-Dimethoxyphenyl)acrylonitrile

To an ice bath cooled stirred suspension of sodium hydride (5.0 mmol) in 20 mL of tetrahydrofuran was added 0.8 mL of diethyl cyanomethylphosphonate dropwise via syringe. The mixture was allowed to warm to room temperature and then 3,4,3',4,'-tetramethoxybenzophenone (1.51 g, 5.00 mmol) and 10 mL of tetrahydrofuran were added. The mixture was stirred for 5 days and then quenched with 100 mL of $H_2O$. The reaction mixture was then extracted with methylene chloride (50 mL and 25 mL). The combined extracts were dried over sodium sulfate and concentrated to afford the crude product as an oil. The crude product was purified by flash chromatography to afford the product as a white wax: $^1$H NMR (CDCl$_3$) δ 7.95 (br m, 6 H), 5.57 (s, 1 H), 3.94 (s, 3 H), 3.92 (s, 3 H), 3.87 (s, 3 H), 3.84 (s, 3 H); $^{13}$C NMR (DMSO-d$_6$) δ 162.4, 151.0, 150.5, 148.8, 148.5, 131.8, 129.5, 123.2, 122.2, 118,6, 112.7, 111.4, 110.7, 110.7, 91.9, 56.0, 55.9, 55.9.

EXAMPLE 2 cis and trans 3-(3,4-Dimethoxyphenyl)-3-(3-ethoxy-4-methoxyphenyl)acrylonitrile

A. 3, 4-Dimethoxy-3-ethoxy-4-methoxybenzophenone

To an ice bath cooled stirred suspension of 3-ethoxy-4-methoxybenzoic acid (0.98 g, 5.0 mmol) in 20 mLmethylene chloride was added oxalyl chloride (0.44 mL, 5.0 mmol) and 2 drops of N,N dimethylformamide (dimethylformamide). The resulting yellow mixture was stirred at room temperature for 35 minutes at which time a solution had formed. The solution was cooled in an ice bath and veratrole (0.64 mL, 5.0 mmol) was added followed by aluminum chloride (0.73 g, 5.5 mmol). The ice bath was removed and the mixture was stirred at room temperature. The reaction was monitored by HPLC (Waters Nova-Pak/C,8 column 3.9×150 mm, 4 micron, 1 mL/min, 35/65 acrylonitrile/0.1% aqueous phosphoric acid and after 37 hours the reaction was complete. The reaction mixture was poured into 30 mL of ice, stirred for 30 minutes and was then extracted with methylene chloride (3×20 mL). The methylene chloride extracts were washed successively with aqueous sodium bicarbonate (30 mL), water (2×50 mL) and brine (50 mL). The organic layer was then dried over magnesium sulfate, filtered and concentrated in vacuo to afford 1.05 g of a brown solid. The crude product was purified by flash column chromatography (silica gel, 5% ethyl acetate/methylene chloride) and the resulting product was then dried in vacuo (60° C., <1 mmHg) to afford 0.8 g (51%) of the product: mp 122–124.5° C.; $^1$H NMR (CDCl3) δ 7.48–7.34 (m, 4 H), 6.98–6.86 (m, 2 H), 4.16 (q, J=7 Hz, 2 H), 3.96 (s, 3 H), 3.96 (s, 3 H), 3.94 (s, 3 H), 1.49 (t, J=7 Hz, 3 H); $^{13}$C NMR (CDCl3) δ 194.4, 152.8, 152.5, 148.8, 148.0, 130.7, 130.6, 124.6, 124.5, 113.5, 112.2, 109.9, 109.7, 64.3, 55.9, 55.9, 14.6; HPLC (Waters Nova-Pak/C,8 column, 3.9×150 mm, 4 micron, 1 mL/min, 35/65 acrylonitrile/0.1% aqueous phosphoric acid 8 min, 99%; Anal. Calcd for $C_{18}H_{20}O_5$. Theoretical: C, 68.34; H, 6.37. Found: C, 68.56; H, 6.51.

B. cis and trans 3-(3,4-Dimethoxyphenyl)-3-(3-ethoxy-4-methoxyphenyl)acrylonitrile To an ice bath cooled stirred solution of diethylcyanomethylphosphonate (0.9 mL, 5.5 mmol) in 15 mL of tetrahydrofuran was added a 1.3 M solution of lithium hexamethyldisilazide (4.2 mL, 5.5 mmol) in tetrahydrofuran. The solution was allowed to warm to room temperature and was stirred for 30 minutes and then a slurry of 3,4-dimethoxy-3-ethoxy-4-methoxybenzophenone (1.58 g, 5.00 mmol) in 20 mL of tetrahydrofuran was added. The reaction mixture was stirred at room temperature for 21 hours and was then quenched with 100 mL of water. The resulting mixture was extracted with methylene chloride (2×50 mL). The combined extracts were washed with water, chied over magnesium sulfate, and concentrated in vacuo to afford the crude product as an orange oil. The crude product was purified by flash column chromatography (silica gel, 3% ethyl acetate/methylene chloride) and then recrystallized from hexane/ethyl. The resulting product was then dried in vacuo (40° C., <1 mmHg) to afford 0.6 g (35%) of a white solid: mp 103–106° C.; $^1$H NMR (CDCl$_3$) δ 7.10–6.75 (m, 6 H), 5.55 (s, 1H), 4.17–3.76 (m, 11 H), 1.54–1.36 (m, 3 H); $^{13}$C NMR (CDCl$_3$) δ 162.5, 151.0, 150.8, 150.5, 148.8, 148.6, 148.1, 147.8, 131.9, 131.7, 129.6, 129.5, 123.2, 123.1, 122.1, 122.0, 118.6, 114.2, 112.9, 112.8, 111.4, 110.9, 110.9, 110.7, 110.7, 91.8, 64.5, 56.0, 55.9, 14.6; HPLC (Waters Nova-Pak/C,8 column, 3.9×150 mm, 4 micron, 1 mL/min, 45/55 acrylonitrile/0.1% aqueous phosphoric acid 7 min, 100%; Anal. Calcd for C$_{20}$H$_{21}$NO$_4$. Theoretical: C, 70.78; H, 6.24; N, 4.13. Found: C, 70.62; H, 6.21; N, 4.07.

EXAMPLE 3

3-(3,4-Dimethoxyphenyl)-3-phenylacetate

A. 3,4-Dimethoxybenzophenone 3,4-Dimethoxybenzophenone was prepared analogously to 3,4,3',4'-tetramethoxybenzophenone using veratrole (2 mL, 15 mmol), aluminum chloride (2.2 g, 16.5 mmol) and benzoyl chloride (1.8 mL, 15.5 mmol). The crude mixture was purified by flash column chromatography (silica gel, 3% ethyl acetate/methylene chloride) to yield 3.44 g (93%) of the product as a white solid: mp 99–100° C.; $^1$H NMR (CDCl$_3$) δ 7.82–7.30 (m, 7 H), 6.95–6.85 (m, 1 H), 3.96 (s, 3 H), 3.94 (s, 3 H); $^{13}$C NMR (CDCl$_3$) δ 195.5, 153.0, 149.0, 138.2, 131.8, 130.2, 129.6, 128.1, 125.4, 112.1, 109.7, 56.0, 56.0; Anal. Calcd for C$_{15}$H$_{14}$O$_3$. Theoretical: C, 74.36; H, 5.82. Found: C, 74.21; H, 6.01.

B. 3-(3,4-Dimethoxyphenyl)-3-phenylacetate (E and Z Isomers)

3-(3,4-Dimethoxyphenyl)-3-phenylacetate was prepared analogously to 3,3-bis-(3,4-dimethoxyphenyl)acrylate using 3,4-dimethoxybenzophenone (4.8 g, 20 mmol), trimethylphosphonoacetate (4.1 g, 22 mmol) and lithium hexamethyldisilazide (22 mL, 22 mmol, 1M) with a reaction time of 138 hours at reflux. The crude mixture was purified by flash column chromatography (silica gel, 1% ethyl acetate/methylene chloride) to afford 14.39 g (73%) of a mixture of the E and Z isomers as an oil. The isomers were separated by additional purification (silica gel, 1% ethyl acetate/methylene chloride) to afford pure samples of each of the isomers.

Isomer 1: $^1$H NMR (CDCl$_3$) δ 7.40–7.36 (m, 3 H), 7.26–7.20 (m, 2 H), 6.88 (s, 1 H), 6.80 (s, 2 H), 6.30 (s, 1 H), 3.88 (s, 3 H), 3.82 (s, 3 H), 3.60 (s, 3 H); $^{13}$C NMR (CDCl$_3$) δ 166.5, 156.9, 150.4, 148.7, 138.9, 133.4, 129.1, 128.1, 128.0, 127.8, 122.1, 114.9, 110.8, 110.6, 55.9, 55.8, 51.1; Anal. Calcd for C$_{18}$H$_{18}$O$_4$. Theoretical: C, 72.47; H, 6.08. Found: C, 72.08; H, 6.11.

Isomer 2: $^1$H NMR (CDCl$_3$) δ 7.35–7.32 (m, 5 H), 6.90–6.83 (m, 2 H), 6.73 (s, 1 H), 6.30 (s, 1 H), 3.92 (s, 3 H), 3.81 (s, 3 H), 3.64 (s, 3 H); $^{13}$C NMR (CDCl$_3$) δ 166.7, 156.7, 149.2, 148.3, 141.2, 131.1, 129.4, 128.5, 128.3, 122.4, 116.4, 112.7, 110.4, 55.8, 55.7, 51.2; Anal. Calcd for C$_{18}$H$_{18}$O$_4$. Theoretical: C, 72.47; H, 6.08. Found: C, 72.28; H, 5.94.

EXAMPLE 4

3-Phenyl-3-(3'-ethoxy-4-methoxyphenyl)acrylamide (E and Z Isomers)

The acrylamide was prepared analogously to 3,3-bis-(3,4-dimethoxyphenyl)acrylate using 3-ethoxy-4-methoxybenzophenone (0.3 g, 1.2 mmol), diethylcarbamoylmethylphosphonate (0.25 g, 1.3 mmol) and lithium hexamethyldisilazide (1 mL, 1.3 mmol, 1.3M) with a reaction time of 54 hours at reflux. The crude mixture was purified by flash column chromatography (silica gel, 45% ethyl acetate/methylene chloride) to afford 0.06 g (17%) of a mixture of the E and Z isomers as an oil: $^1$H NMR (CDCl$_3$) δ 7.54–7.19 (m, 10 H), 7.00–6.65 (m, 6 H), 6.34 (s, 2 H), 5.54 (s, 1 H), 5.55 (s, 1 H), 5.24 (s, 1 H), 5.04 (s, 1 H), 4.16 (m, 4 H), 3.92 (s, 3 H), 3.87 (s, 3 H), 1.60–1.33 (m, 6 H); $^{13}$C NMR (CDCl$_3$) δ 168.7, 168.6, 150.8, 150.4, 149.7, 148.4, 148.0, 140.7, 138.2, 133.0, 130.2, 129.2, 129.1, 128.8, 128.3, 128.0, 121.9, 121.6, 120.0, 113.7, 111.9, 111.4, 110.8, 64.4, 64.3, 55.9, 14.6; Anal. Calcd for C$_{18}$H$_{19}$NO$_3$· 0.35H$_2$O. Theoretical: C, 71.19; H, 6.54; N, 4.61. Found: C, 71.19; H, 6.68; N, 4.45.

EXAMPLE 5

1-(3,4-Dimethoxyphenyl)-1-phenylprop-1-ene (E and Z Isomers)

1-(3,4-Dimethoxyphenyl)-1-phenylprop-1-ene was prepared analogously to methyl 3,3-bis-(3,4-dimethoxyphenyl) acrylate using 3,4-dimethoxybenzophenone (3 g, 12.4 mmol), (ethyl)triphenylphosphonium bromide (5.1 g, 13.6 mmol) and lithium hexamethyldisilazide (13.6 mL, 13.6 mmol, 1M) with a reaction time of 4 hours at room temperature. The crude mixture was purified by flash column chromatography (silica gel, 10% hexane/methylene chloride) to afford 1.3 g (41%) of a mixture of the E and Z isomers as a white solid: mp 72–73° C.; $^1$H NMR (CDCl$_3$) δ 7.40–6.80 (m, 16 H), 6.16–6.08 (m, 2 H), 3.90–3.80 (m, 12 H), 1.97–1.73 (m, 6 H); $^{13}$C NMR (CDCl$_3$) δ 148.6, 148.5, 148.1, 147.8, 142.9, 142.3, 142.0, 140.0, 136.0, 132.5, 129.9, 128.0, 128.0, 127.1, 126.7, 126.6, 123.8, 122.6, 122.5, 119.8, 113.6, 110.8, 110.7, 110.4, 55.8, 55.8, 55.7, 15.7, 15.5; Anal. Calcd for C$_{17}$H$_{18}$O$_2$. Theoretical: C, 80.28; H, 7.13. Found: C, 79.94; H, 7.12.

EXAMPLE 6

1-(3,4-Dimethoxyphenyl)-1-(3-ethoxy-4-methoxyphenyl)prop-1-ene (E and Z Isomers)

1-(3,4-Dimethoxyphenyl)-1-(3-ethoxy-4-methoxyphenyl)prop-1-ene was prepared analogously to methyl 3,3-bis-(3,4-dimethoxyphenyl)acrylate using 3,4-dimethoxy-3'-ethoxy-4'-methoxybenzophenone (1.6 g, 5 mmol), (ethyl)triphenylphosphonium bromide (2.04 g, 5.5 mmol) and lithium hexamethyldisilazide (4.2 mL, 5.5 mmol, 1.3M) with a reaction time of 24 hours at room temperature. The crude mixture was purified by flash column chromatography (silica gel, 10% hexane/methylene chloride) to afford 0.8 g (49%) of a mixture of the E and Z isomers as a white solid: mp 65.5–68° C.; $^1$H NMR (CDCl$_3$) δ 6.95–6.65 (m, 12 H), 6.14–6.00 (m, 2 H), 4.11–3.78 (m, 22 H), 1.86–1.74 (m, 6 H), 1.50–1.36 (m, 6 H); $^{13}$C NMR (CDCl$_3$) δ 148.5, 148.4, 148.1, 147.7, 141.8, 141.7, 136.1, 136.0, 132.6, 132.5, 122.5, 122.3, 119.7, 114.7, 113.1, 111.9, 111.0, 110.7, 110.4, 55.9, 55.8, 55.8, 55.7, 15.7, 14.7; Anal. Calcd for C$_{20}$H$_{24}$O$_4$. Theoretical: C, 73.15; H, 7.37. Found: C, 73.33; H, 7.39.

EXAMPLE 7

1-(3,4-Dimethoxyphenyl)-1-(3-ethoxy-4-methoxyphenyl)but-1-ene (E and Z Isomers)

1-(3,4-Dimethoxyphenyl)-1-(3-ethoxy-4-methoxyphenyl)but-1-ene was prepared analogously to methyl 3,3-bis-(3,4-dimethoxyphenyl)acrylate using 3,4-dimethoxy-3'-ethoxy-4'-methoxybenzophenone (1 g, 3.2 mmol), propyltriphenylphosphonium bromide (1.34 g, 3.5 mmol) and lithium hexamethyldisilazide (2.7 mL, 3.5 mmol, 1.3M) with a reaction time of 2.5 hours at room temperature. The crude mixture was purified by chromatography (silica gel, methylene chloride) followed by a Kugelrohr distillation to yield 0.77 g (71%) of a mixture of the E and Z isomers as an oil: H NMR (CDCl$_3$) δ 6.92–6.65 (m, 12 H), 6.02–5.89 (m, 2 H), 4.12–3.96 (m, 4 H), 3.92 (s, 3 H), 3.91 (s, 3 H), 3.86 (s, 3 H), 3.85 (s, 3 H), 3.82 (s, 3 H), 3.81 (s, 3 H), 2.22–2.04 (m, 4 H), 1.51–1.38 (m, 6 H), 1.14–0.98 (m, 6 H); $^{13}$C NMR (CDCl$_3$) δ 148.5, 148.1, 147.8, 147.7, 140.4, 140.4, 136.0, 135.9, 133.0, 132.9, 130.1, 130.0, 122.2, 119.8, 114.6, 113.1, 112.0, 111.0, 110.7, 110.4, 64.3, 64.2, 55.9, 23.2, 14.8, 14.7; Anal. Calcd for C$_{21}$H$_{26}$O$_4$. Theoretical: C, 73.66; H, 7.65. Found: C, 73.32; H, 7.26.

EXAMPLE 8

3-(3-Ethoxy-4-methoxyphenyl)-3-phenylacrylonitrile (E and Z Isomers)

3-(3-Ethoxy-4-methoxyphenyl)-3-phenylacrylonitrile was prepared analogously to 3,3-bis-(3,4-dimethoxyphenyl) acrylate using 3-ethoxy-4-methoxybenzophenone (1.3 g, 5 mmol), diethylcyanomethylphosphonate (0.9 mL, 5.5 mmol) and lithium hexamethyldisilazide (4.2 mL, 5.5 mmol, 1.3M) with a reaction time of 24 hours at room temperature. The crude mixture was purified by flash column chromatography (silica gel, methylene chloride) to afford 1.35 g (96%) of a mixture of the E and Z isomers as a white solid: mp 74–77° C.; $^1$H NMR (CDCl$_3$) δ 7.50–7.24 (m, 10 H), 7.07–6.75 (m, 6 H), 5.67 (s, 1 H), 5.60 (s, 1 H), 4.15–3.95 (m, 4 H), 3.92 (s, 3 H), 3.89 (s, 3 H), 1.50–1.36 (m, 6 H) $^{13}$C NMR (CDCl$_3$) δ 162.8, 162.7, 151.4, 150.9, 148.1, 147.1, 147.9, 139.3, 137.1, 131.3, 130.2, 129.9, 129.5, 129.3, 128.6, 128.5, 128.4, 123.1, 122.0, 118.3, 118.2, 113.9, 112.5, 110.9, 93.3, 92.9, 64.4, 55.9, 55.9, 14.6; Anal. Calcd for C$_{18}$H$_{17}$NO$_2$. Theoretical: C, 77.40; H, 6.13; N, 5.01. Found: C, 77.14; H, 6.06; N, 4.75.

EXAMPLE 9

3-(3-Ethoxy-4-methoxyphenyl)-3-phenylpropionitrile

To a solution of 3-(3-ethoxy-4-methoxyphenyl)-3-phenylacrylonitrile (0.9 g, 3.2 mmol) in a mixture of ethanol and ethyl acetate (20 mL/ 30 mL) was added 0.5 g of 10% palladium on carbon catalyst in portions. The mixture was hydrogenated in a Parr-Shaker apparatus at 55–60 psi of hydrogen for 12 days. The reaction mixture was filtered through celite and the filtrate was concentrated in vacuo to afford the crude product. The crude product was purified by flash column chromatography (silica gel, 4% hexane/methylene chloride) to afford 0.15 g (15%) of the product as an oil: $^1$H NMR (CDCl$_3$) δ 7.40–7.16 (m, 5 H); 6.88–6.78 (m, 3 H), 4.32 (t, J=7.5 Hz, 1 H), 4.03 (q, J=7 Hz, 2 H), 3.85 (s, 3 H), 3.00 (d, J=7.5 Hz, 2 H), 1.42 (t, J=7 Hz, 3 H); $^{13}$C NMR (CDCl$_3$) δ 148.7, 148.5, 141.5, 133.7, 128.8, 127.4, 127.3, 119.5, 118.5, 112.7, 111.6, 64.4, 55.9, 46.7, 24.5, 14.7; Anal. Calcd for C$_{18}$H$_{17}$NO$_2$. Theoretical: C, 76.84; H, 6.81; N, 4.98. Found: C, 76.53; H, 6.92; N, 4.95.

EXAMPLE 10

3-(3,4-Dimethoxyphenyl)-3-(3',5'-dimethoxyphenyl) acrylonitrile (E and Z Isomers)

A. 3,4,3',5'-Tetramethoxybenzophenone 3,4,3',5'-Tetramethoxybenzophenone was prepared analogously to 4-(3,4-dimethoxybenzoyl)pyridine using butyl lithium (9 mL, 22 mmol, 2.5M), 4-bromoveratrole (2.9 mL, 20 mmol) and 3,5-dimethoxybenzonitrile (3.75 g, 23 mmol). The crude product was purified by flash column chromatography (silica gel, methylene chloride) to afford 1.54 g (26%) of the product: mp 107–110° C.; $^1$H NMR (CDCl$_3$) δ 7.53–7.39 (m, 2 H), 6.95–6.84 (m, 3 H), 6.70–6.60 (m, 1 H), 3.96 (s, 3 H), 3.95 (s, 3 H), 3.83 (s, 6 H); $^{13}$C NMR (CDCl$_3$) δ 195.0, 160.4, 153.0, 148.9, 140.1, 130.0, 125.4, 112.0, 109.7, 107.5, 104.1, 56.0, 55.5; Anal. Calcd for C$_{17}$H$_{18}$O$_5$. Theoretical: C, 67.54; H, 6.00. Found: C, 67.38; H, 5.96.

B. 3-(3,4-Dimethoxyphenyl)-3-(3',5'-dimethoxyphenyl) acrylonitrile 3-(3,4-Dimethoxyphenyl)-3-(3',5'-dimethoxyphenyl) acrylonitrile was prepared analogously to methyl 3,3-bis-(3, 4-dimethoxyphenyl)acrylate using 3,4,3',5'-tetramethoxybenzophenone (0.7 g, 2.3 mmol), diethylcyanomethylphosphonate (0.42 mL, 2.5 mmol) and lithium hexamethyldisilazide (1.9 mL, 2.5 mmol, 1.3M) with a reaction time of 60 hours at room temperature. The crude product was purified by flash chromatography (silica gel, 1% ethyl acetate/methylene chloride) to afford 0.66 g (81%) of a mixture of the E and Z isomers as a white solid: mp 88–90° C.; $^1$H NMR (CDCl$_3$) δ 7.10–6.80 (m, 6 H), 6.61–6.40 (m, 6 H), 5.66 (s, 1 H), 5.61 (s, 1 H), 3.94 (s, 3 H), 3.91 (s, 3 H), 3.87 (s, 3 H), 3.84 (s, 3 H), 3.80 (s, 3 H), 3.77 (s, 6 H); $^{13}$C NMR (CDCl$_3$) δ 162.7, 162.5, 160.7, 160.6, 151.1, 150.6, 148.8, 148.5, 141.3, 138.9, 131.1, 129.2, 123.2, 122.1, 118.2, 118.0, 112.6, 110.9, 110.7, 110.7, 107.6, 107.0, 102.1, 102.0, 93.4, 93.1, 56.0, 55.9, 55.5, 55.4; Anal. Calcd for C$_{19}$H$_{19}$NO$_4$. Theoretical: C, 70.14; H, 5.89; N, 4.30. Found: C, 70.33; H, 5.89; N, 4.03.

EXAMPLE 11

3-(3,4-Dimethoxyphenyl)-3-(3'-nitrophenyl) acrylonitrile

A. 3,4-Dimethoxy-3'-nitrobenzophenone

To a stirred ice bath cooled solution of veratrole (2.55 mL, 20 mmol) in methylene chloride (30 mL) under nitrogen was added aluminum chloride (2.93 g, 22 mmol). A slight exotherm resulted. To the resulting mixture was added 3-nitrobenzoyl chloride (3.8 g, 20 mmol) in 30 mL of methylene chloride. The reaction was then allowed to warm to room temperature and followed by heating to refluxed. After 5 hours at reflux the reaction mixture was allowed to cool to room temperature and stirred for 72 hours. The reaction mixture was then poured into 100 mL of iced water and stirred for 20 minutes. This mixture was extracted with CH$_2$Cl$_2$ (3×60 mL). The organic layer was dried over magnesium sulfate and concentrated in vacuo to afford the crude product as a green solid. The crude product was purified by flash column chromatography (silica gel, CH$_2$Cl$_2$) to afford 2.21 g (39%) of the product as a yellow solid: mp 133–135° C.; $^1$H NMR (CDCl$_3$) δ 8.64–8.56 (m, 1 H), 8.49–8.39 (m, 1 H), 8.10–8.05 (m, 1 H), 7.76–7.65 (m, 1H), 7.55–7.47 (m, 1 H), 7.36–7.29 (m, 1 H), 7.00–6.87 (m, 1 H), 3.99 (s, 3 H), 3.97 (s, 3 H); $^{13}$C NMR (CDCl$_3$) δ 192.8, 153.8, 149.4, 147.9, 139.7, 135.2, 129.5, 128.9, 126.2, 125.6, 124.4, 11.8, 110.0, 56.2, 56.1; Anal. Calcd for C$_{15}$H$_{13}$NO$_5$. Theoretical: C, 62.72; H, 4.56; N, 4.88. Found: C, 62.74; H, 4.59; N, 4.89.

B. 3-(3,4-Dimethoxyphenyl)-3-(3'-nitrophenyl)acrylonitrile 3-(3,4-Dimethoxyphenyl)-3-(3'-nitrophenyl)acrylonitrile was prepared analogously to methyl 3,3-bis-(3,4-dimethoxyphenyl)acrylate using 3,4-dimethoxy-3'nitrobenzophenone (1.44 g, 5 mmol), diethylcyanomethylphosphonate (0.91 mL, 5.5 mmol) and lithium hexamethyldisilazide (4.2 mL, 5.5 mmol, 1.3M) with a reaction time of 24 hours at room temperature. The crude product was purified by flash chromatography (silica gel, 3% hexane/methylene chloride) to afford 1.12 g (72%) of a mixture of the E and Z isomers as a yellow solid: mp 117.5–120° C.; $^1$H NMR (CDCl$_3$) δ 8.40–8.17 (m, 4 H), 7.90–7.55 (m, 4 H), 7.08–6.89 (m, 6 H), 5.84 (s, 1 H), 5.71 (s, 1 H), 3.95 (s, 3 H), 3.92 (s, 3 H), 3.88 (s, 3 H), 3.85 (s, 3 H); $^{13}$CNMR (CDCl$_3$) δ 160.2, 160.1, 151.7, 151.1, 149.2, 148.3, 148.2, 141.0, 138.8, 135.4, 134.4, 129.9, 129.7, 129.7, 128.1, 124.8, 124.6, 124.4, 123.3, 123.1, 122.3, 117.4, 117.3, 112.3, 111.0, 110.4, 95.7, 94.8, 56.0, 55.9; Anal. Calcd for $C_{17}H_{14}N_2O_4$. Theoretical: C, 65.80; H, 4.55; N, 9.03. Found: C, 65.57; H, 4.64; N, 8.92.

EXAMPLE 12

3-(3'-Aminophenyl)-3-(3,4-dimethoxyphenyl) acrylonitrile (E and Z Isomers)

To a solution of 3-(3,4-dimethoxyphenyl)-3-(3'-nitrophenyl)acrylonitrile (0.7 g, 2.3 mmol) in 40 mL of ethyl acetate was added 0.1 g of 10% palladium on carbon catalyst. The mixture was hydrogenated in a Parr-Shaker apparatus at 55–60 psi of hydrogen for 2.5 hours. The reaction mixture was filtered through celite and the filtrate was concentrated in vacuo to afford the crude product. The crude product was purified by flash column chromatography (silica gel, 15% ethyl acetate/methylene chloride) to afford 0.25 g (56%) of a mixture of the E and Z isomers as a yellow solid: mp 100–101° C.; $^1$H NMR (CDCl$_3$) δ 7.30–6.59 (m, 14 H); 5.63 (s, 1 H), 5.59 (s, 1 H), 3.94 (s, 3 H), 3.91 (s, 3 H), 3.87 (s, 3 H), 3.84 (s, 3 H); $^{13}$C NMR (CDCl$_3$) δ 163.1, 162.9, 151.1, 150.5, 148.8, 148.7, 146.5, 146.4, 140.4, 138.2, 131.5, 129.5, 129.5, 129.4, 123.2, 122.1, 119.9, 119.0, 118.4, 118.2, 116.8, 116.6, 115.9, 115.0, 112.7, 111.0, 110.7, 93.3, 92.7, 56.1, 56.0, 55.9; Anal. Calcd for $C_{17}H_{16}N_2O_3$. Theoretical: C, 72.84; H, 5.75; N, 9.99. Found: C, 72.48; H, 6.05; N, 9.58.

EXAMPLE 13

3,4-Dimethoxy-3'-aminobenzophenone

To a solution of 3,4-dimethoxy-3'-nitrobenzophenone (0.5 g, 1.7 mmol) in 40 mL of ethyl acetate was added 0.05 g of 10% palladium on carbon catalyst. The mixture was hydrogenated in a Parr-Shaker apparatus at 55–60 psi of hydrogen for 1.5 hours. The reaction mixture was filtered through celite and the filtrate was concentrated in vacuo to afford the crude product. The crude product was purified by flash column chromatography (silica gel, 10% ethyl acetate/ methylene chloride) to afford 0.17 g (38%) of the product as a yellow solid: mp 157–175° C.; $^1$H NMR (CDCl$_3$) δ 7.56–6.80 (m, 7 H); 3.95 (s, 3 H), 3.94 (s, 3 H); $^{13}$C NMR (CDCl$_3$) δ 195.7, 152.9, 148.9, 146.4, 139.3, 130.3, 128.9, 125.4, 120.1, 118.4, 115.6, 112.1, 109.7, 56.0, 56.0; Anal. Calcd for $C_{15}H_{15}NO_3$. Theoretical: C, 70.02; H, 5.88; N, 5.44. Found: C, 70.00; H, 6.10; N, 5.13.

EXAMPLE 14

3-(3,4-Dimethoxyphenyl)-3-(4-nitrophenyl) acrylonitrile (E and Z Isomers)

A. 3,4-Dimethoxy-4'-nitrobenzophenone 3,4-Dimethoxy-4'-nitrobenzophenone was prepared analogously to 3,4-dimethoxy-3'-nitrobenzophenone using veratrole (3.8 mL, 30 mmol), aluminum chloride (4.4 g, 33 mmol) and 4-nitrobenzoyl chloride (5.7 g, 30 mmol) with a reaction time of 48 hours at reflux. The crude mixture was purified by flash column chromatography (silica gel, 4% ethyl acetate/methylene chloride) to afford 1.69 g (78%) of the product as a white solid: mp 172–173° C.; $^1$H NMR (CDCl$_3$) δ 8.43–8.31 (m, 2 H), 7.97–7.86 (m, 2 H), 7.55–7.46 (m, 1 H), 7.40–7.30 (m, 1 H), 7.00–6.89 (m, 1 H), 3.99 (s, 3 H), 3.96 (s, 3 H), $^{13}$C NMR (CDCl$_3$) δ 193.4, 153.8, 149.4, 149.3, 143.8, 130.2, 130.0, 125.8, 123.4, 111.7, 109.9, 56.1, 56.0; Anal. Calcd for $C_{15}H_{13}NO_5$. Theoretical: C, 62.72; H, 4.56; N, 4.88. Found: C, 62.49; H, 4.68; N, 4.86.

B. 3-(3,4-Dimethoxyphenyl)-3-(4'-nitrophenyl)acrylonitrile 3-(3,4-Dimethoxyphenyl)-3-(4'-nitrophenyl)acrylonitrile was prepared analogously to methyl 3,3-bis-(3',4'-dimethoxyphenyl)acrylate using 3,4-dimethoxy-4'nitrobenzophenone (4 g, 14 mmol), diethylcyanomethylphosphonate (2.5 mL, 15.4 mmol) and lithium hexamethyldisilazide (11.8 mL, 15.4 mmol, 1.3M) with a reaction time of 17 hours at room temperature. The crude product was purified by chromatography (silica gel, 3% hexane/methylene chloride) to afford 2.38 g (55%) of a mixture of the E and Z isomers as a yellow solid: mp 117.5–120° C.; $^1$H NMR (CDCl$_3$) δ 8.40–8.20 (m, 4 H), 7.70–7.46 (m, 4 H), 7.06–6.75 (m, 6 H), 5.84 (s, 1 H), 5.70 (s, 1 H), 3.95 (s, 3 H), 3.93 (s, 3 H), 3.88 (s, 3 H), 3.85 (s, 3 H); $^{13}$C NMR (CDCl$_3$) δ 160.3, 151.7, 151.1, 149.2, 148.9, 148.7, 148.5, 148.5, 143.5, 130.6, 129.9, 129.6, 128.2, 123.7, 123.1, 122.2, 117.4, 117.3, 112.3, 111.0, 110.5, 96.2, 94.9, 56.0, 56.0; Anal. Calcd for $C_{17}H_{14}N_2O_4$. Theoretical: C, 65.80; H, 4.55; N, 9.03. Found: C, 65.45; H, 4.66; N, 8.82.

EXAMPLE 15

3-(4-Aminophenyl)-3-(3,4-dimethoxyphenyl) acrylonitrile 3-(4-Aminophenyl)-3-(3,4-dimethoxyphenyl) acrylonitrile was prepared analogously to 3-(3,4-dimethoxyphenyl)-3-(3-aminophenyl)acrylonitrile using 3-(3,4-dimethoxyphenyl)-3-(4-nitrophenyl)acrylonitrile (1.24 g, 4 mmol) and 0.15 g of 10% palladium on carbon catalyst in 100 mL of ethyl acetate. The crude mixture was purified by flash column chromatography (silica gel, 5% ethyl acetate/methylene chloride) to afford 0.19 g (17%) of a mixture of the E and Z isomers as a yellow solid: mp 150–152° C.; $^1$H NMR (CDCl$_3$) δ 7.38–6.56 (m, 14 H); 5.51 (s, 1 H), 5.44 (s, 1 H), 3.97 (br s, 4 H), 3.93 (s, 3 H), 3.91 (s, 3 H), 3.85 (s, 3 H), 3.82 (s, 3 H); $^{13}$C NMR (CDCl$_3$) δ 162.8, 162.6, 150.8 148.8, 148.7, 148.5, 148.4, 132.4, 131.4, 130.1, 129.5, 129.9, 128.6, 126.7, 123.0, 122.1, 114.4, 114.3, 112.8, 111.6, 110.7, 90.3, 89.9, 56.0, 55.9; Anal. Calcd for $C_{17}H_{16}N_2O_3$. Theoretical: C, 72.84; H, 5.75; N, 9.99. Found: C, 72.79; H, 5.83; N, 9.59.

EXAMPLE 16

3,4-Dimethoxy-4'-aminobenzophenone 3,4-Dimethoxy-4'-aminobenzophenone was prepared analogously to 3,4-dimethoxy-3'-aminobenzophenone using 3,4-dimethoxy-4'-nitrobenzophenone (1 g, 3.5 mmol) and 0.1 g of 10% palladium on carbon catalyst in 110 mL of ethyl acetate. The crude product was purified by flash column chromatography (silica gel, 12% ethyl acetate/methylene chloride) to afford 0.32 g (36%) of the product as a yellow solid: mp 189–191° C.; $^1$H NMR (CDCl$_3$) δ 7.80–7.62 (m, 2 H); 7.45–7.29 (m, 2 H), 6.96–6.80 (m, 1 H), 6.75–6.61 (m, 2 H), 4.14 (s, 2 H), 3.95 (s, 3 H), 3.93 (s, 3 H); $^{13}$C NMR (CDCl$_3$) δ 194.2, 152.2, 150.5, 148.8, 132.6, 131.3, 128.0, 124.3, 113.6, 112.3, 109.7, 56.0; Anal. Calcd for C$_{15}$H$_{15}$NO$_3$. Theoretical: C, 70.02; H, 5.88; N, 5.44. Found: C, 69.95; H, 6.18; N, 5.13.

EXAMPLE 17

3-(3,4-Dimethoxyphenyl)-3-(4-methylphenyl)acrylonitrile

A. 3,4-Dimethoxy-4'-methylbenzophenone

The title compound was prepared analogously to 3,4,3',4'-tetramethoxybenzophenone using veratrole (3.9 mL, 28 mmol), aluminum chloride (4.1 g, 31 mmol) and 4-methylbenzoyl chloride (4.6 mL, 29 mmol) with a reaction time of 6 hours at room temperature. The crude mixture was purified by flash column chromatography (silica gel, 2% ethyl acetate/methylene chloride) to afford 4.22 g (59%) of the product as a white solid: mp 121.5–122° C.; $^1$H NMR (CDCl$_3$) δ 7.70–7.67 (d, J=8 Hz, 2 H), 7.48–7.26 (m, 4 H), 6.91–6.88 (d, J=8.3 Hz, 1 H), 6.96 (s, 3 H), 3.94 (s, 3 H), 2.44 (s, 3 H); $^{13}$C NMR (CDCl$_3$) δ 195.1, 152.6, 148.8, 142.4, 135.3, 130.3, 129.8, 128.7, 125.0, 112.0, 109.6, 55.9, 55.8, 21.4; Anal. Calcd for C$_{16}$H$_{16}$O$_3$. Theoretical: C, 74.98; H, 6.29. Found: C, 74.84; H, 6.43.

B. 3-(3,4-Dimethoxyphenyl)-3-(4-methylphenyl)acrylonitrile 3-(3,4-Dimethoxyphenyl)-3-(4-methylphenyl)acrylonitrile was prepared analogously to methyl 3,3-bis-(3,4-dimethoxyphenyl)acrylate using 3,4-dimethoxy-4'-methylbenzophenone (2.3 g, 9 mmol), diethylcyanomethylphosphonate (1.8 mL, 9.9 mmol) and lithium hexamethyldisilazide (10 mL, 9.9 mmol, 1M) with a reaction time of 22 hours at room temperature. The crude product was purified by chromatography (silica gel, 1% ethyl acetate/methylene chloride) to afford 1.83 g (73%) of a mixture of the E and Z isomers as a white solid: mp 83.5–86.5° C.; $^1$H NMR (CDCl$_3$) δ 7.35–7.20 (m, 8 H), 7.04–6.81 (m, 6 H), 5.62 (s, 1 H), 5.59 (s, 1 H), 3.90 (s, 3 H), 3.90 (s, 3 H), 3.88 (s, 3 H), 3.82 (s, 3 H), 2.41 (s, 3 H), 2.39 (s, 3 H); $^{13}$C NMR (CDCl$_3$) δ 162.7, 162.6, 160.0, 150.4, 148.8, 148.5, 140.6, 140.1, 136.3, 134.1, 131.6, 129.5, 129.2, 129.0, 128.5, 123.0, 122.1, 118.4, 118.3, 112.6, 111.1, 110.7, 92.6, 92.4, 55.9, 55.9, 55.8, 21.3, 21.2; Anal. Calcd for C$_{18}$H$_{17}$NO$_2$. Theoretical: C, 77.40; H, 6.13; N, 5.01. Found: C, 77.64; H, 5.93; N, 5.01.

EXAMPLE 18

3-(4-Biphenylyl)-3-(3,4-dimethoxyphenyl)acrylonitrile

A. 3,4-Dimethoxy-4'-phenylbenzophenone 3,4-Dimethoxy-4'-phenylbenzophenone was prepared analogously to 3,4,3',4'-tetramethoxybenzophenone using veratrole (2.4 g, 17 mmol), aluminum chloride (2.5 g, 19 mmol) and 4-biphenylcarbonyl chloride (4 g, 18 mmol) with a reaction time of 24 hours at room temperature. The crude product was purified by flash column chromatography (silica gel, 2% ethyl acetate/methylene chloride) to afford 3.86 g (70%) of the product as a white solid: mp 103–104° C.; $^1$H NMR (CDCl$_3$) δ 7.88–7.84 (m, 2 H), 7.73–7.64 (m, 4 H), 7.52–7.40 (m, 5 H), 6.93–6.90 (m, 1 H), 3.97 (s, 3 H), 3.96 (s, 3 H); $^{13}$C NMR (CDCl$_3$) δ 194.9, 152.9, 148.9, 144.5, 139.8, 136.8, 130.2, 130.2, 128.8, 127.9, 127.1, 126.7, 125.2, 112.0, 109.7, 55.9, 55.9; Anal. Calcd for C$_{21}$H$_{18}$O$_3$. Theoretical: C, 79.23; H, 5.70. Found: C, 78.91; H, 5.87.

B. 3-(4-Biphenylyl)-3-(3,4-dimethoxyphenyl)acrylonitrile 3-(4-Biphenylyl)-3-(3,4-dimethoxyphenyl)acrylonitrile was prepared analogously to methyl 3,3-bis-(3',4'-dimethoxyphenyl)acrylate using 3,4-dimethoxy-4'-phenylbenzophenone (2.33 g, 7.32 mmol), diethylcyanomethylphosphonate (1.5 mL, 8.1 mmol) and lithium hexamethyldisilazide (8.1 mL, 8.1 mmol, 1M) with a reaction time of 22 hours. The crude product was purified by chromatography (silica gel, 1% ethyl acetate/methylene chloride) to afford 1.76 g (70%) of a mixture of the E and Z isomers as a white solid: mp 132.0–134° C.; $^1$H NMR (CDCl$_3$) δ 7.70–7.39 (m, 18 H), 7.10–6.80 (m, 6 H), 5.69 (s, 1 H), 5.68 (s, 1 H), 3.95 (s, 6 H), 3.93 (s, 3 H), 3.89 (s, 3 H), 3.85 (s, 3 H); $^{13}$C NMR (CDCl$_3$) δ 162.2, 151.1, 148.8, 148.6, 143.0, 142.6, 140.0, 137.9, 135.9, 131.4, 130.1, 129.3, 129.1, 128.8, 128.8, 127.9, 127.1, 127.0, 126.0, 126.9, 123.1, 122.2, 118.3, 118.2, 112.6, 111.1, 110.7, 93.2, 92.9, 56.0, 55.9, 55.8; Anal. Calcd for C$_{23}$H$_{19}$NO$_2$. Theoretical: C, 80.92; H, 5.61; N, 4.10. Found: C, 80.55; H, 5.80; N, 3.95.

EXAMPLE 19

3-(3,4-Dimethoxyphenyl)-3-(4'-fluorophenyl)acrylonitrile 3-(3,4-Dimethoxyphenyl)-3-(4'-fluorophenyl)acrylonitrile was prepared analogously to methyl 3,3-bis-(3,4-dimethoxyphenyl)acrylate using 3,4-dimethoxy-4'-fluorobenzophenone (1.3 g, 5 mmol), diethylcyanomethylphosphonate (0.91 mL, 5.5 mmol) and lithium hexamethyldisilazide (5.5 mL, 5.5 mmol, 1M) with a reaction time of 22 hours at room temperature. The crude product was purified by chromatography (silica gel, 1% ethyl acetate/methylene chloride) to afford 2.38 g (55%) of a mixture of the E and Z isomers as a white solid: mp 100–102° C.; $^1$H NMR (CDCl$_3$) δ 7.54–6.74 (m, 14 H), 5.67 (s, 1 H), 5.57 (s, 1 H), 3.94 (s, 3 H), 3.92 (s, 3 H), 3.87 (s, 3 H), 3.83 (s, 3 H), $^{13}$C NMR (CDCl$_3$) δ 166.0, 165.6, 162.0, 161.6, 151.3, 150.7, 148.9, 148.7, 135.4, 135.4, 133.2, 133.1, 131.7, 131.6, 131.3, 130.7, 130.5, 129.2, 123.1, 122.1, 118.1, 118.0, 115.8, 115.8, 115.5, 115.4, 112.6, 111.0, 110.8, 93.4, 93.2, 56.0, 56.0, 55.9; Anal. Calcd for C$_{17}$H$_{14}$FNO$_2$. Theoretical: C, 72.07; H, 4.98; N, 4.94. Found: C, 71.91; H, 4.98; N, 4.79.

EXAMPLE 20

3-(3,4-Dimethoxyphenyl)-3-naphth-2-ylacrylonitrile (E and Z Isomers)

A. 2-(3,4-Dimethoxybenzoyl)naphthalene 2-(3,4-Dimethoxybenzoyl)naphthalene was prepared analogously to 3,4,3',4'-tetramethoxybenzophenone using veratrole (2.6 mL, 20 mmol), aluminum chloride (2.9 g, 22 mmol) and 2-naphthoyl chloride (3.9 g, 20 mmol) with a reaction time of 4 hours at reflux. The crude product was purified by flash column chromatography (silica gel, 2.5% ethyl acetate/methylene chloride) to afford 4.52 g (77%) of the product as a white solid: mp 120–121.5° C.; $^1$H NMR (CDCl$_3$) δ 8.24 (s, 1 H), 8.03–7.84 (m, 4 H), 7.68–7.40 (m, 4 H), 7.00–6.87 (m, 1 H), 3.97 (s, 3 H), 3.95 (s, 3 H); $^{13}$C NMR (CDCl$_3$) δ 195.5, 153.0, 149.0, 135.5, 134.9, 132.2, 131.0, 130.4, 129.2, 128.1, 128.0, 127.8, 126.7, 125.9, 125.4, 112.2, 109.8, 56.1, 56.0; Anal. Calcd for $C_{19}H_{16}O_3$. Theoretical: C, 78.06; H, 5.52. Found: C, 77.73; H, 5.69.

B. 3-(3,4-Dimethoxyphenyl)-3-naphth-2-ylacrylonitrile 3-(3,4-Dimethoxyphenyl)-3-naphth-2-ylacrylonitrile was prepared analogously to methyl 3,3-bis-(3',4'-dimethoxyphenyl)acrylate using 2-(3,4-dimethoxybenzoyl) naphthalene (2.9 g, 10 mmol), diethylcyanomethylphosphonate (1.8 mL, 11 mmol) and lithium hexamethyldisilazide (8.5 mL, 11 mmol, 1.3M) with a reaction time of 1 hour at reflux. The crude product was purified by chromatography (silica gel, methylene chloride) to afford 2.93 g (93%) of a mixture of the E and Z isomers as a white solid: mp 121–123° C.; $^1$H NMR (CDCl$_3$) δ 8.11–6.78 (m, 20 H), 5.76 (s, 1 H), 5.75 (s, 1 H), 3.96 (s, 3 H), 3.92 (s, 3 H), 3.85 (s, 3 H), 3.80 (s, 3 H); $^{13}$C NMR (CDCl$_3$) δ 162.7, 162.7, 151.2, 150.6, 148.9, 148.7, 136.6, 134.5, 134.0, 133.8, 132.8, 131.5, 129.7, 129.4, 129.0, 128.6, 128.6, 128.3, 128.1, 127.7, 127.7, 127.4, 127.2, 126.8, 126.6, 125.4, 123.2, 122.2, 118.4, 118.2, 112.7, 111.1, 110.8, 93.9, 93.4, 56.0, 56.0, 55.9; Anal. Calcd for $C_{21}H_{17}NO_2$. Theoretical: C, 79.98; H, 5.43; N, 4.44. Found: C, 79.90; H, 5.65; N, 4.46.

EXAMPLE 21

3-(3,4-Dimethoxyphenyl)-3-(3,4-methylenedioxyphenyl)acrylonitrile (E and Z Isomers)

A. 1-(3,4-Dimethoxybenzoyl)-3,4-methylenedioxybenzene 1-(3,4-Dimethoxybenzoyl)-3,4-methylenedioxybenzene was prepared analogously to 3,4,3',4'-tetramethoxybenzophenone using veratrole (1.3 mL, 10 mmol), aluminum chloride (1.5 g, 11 mmol) and piperonyloyl chloride (1.9 g, 10 mmol) with a reaction time of 2.5 hours at room temperature. The crude product was purified by flash column chromatography (silica gel, 5% ethyl acetate/methylene chloride) to afford 1.99 g (69%) of the product as a white solid: mp 164–165° C.; $^1$H NMR (CDCl$_3$) δ 7.46–7.26 (m, 4 H), 6.95–6.82 (m, 2 H), 6.06 (s, 2 H), 3.96 (s, 3 H), 3.94 (s, 3 H); $^{13}$C NMR (CDCl$_3$) δ 193.9, 152.7, 151.0, 148.9, 147.8, 132.4, 130.6, 126.1, 124.8, 112.2, 109.9, 109.7, 107.6, 101.7, 56.0, 56.0; Anal. Calcd for $C_{16}H_{14}O_5$. Theoretical: C, 67.13; H, 4.93. Found: C, 66.86; H, 5.11.

B. 3-(3,4-Dimethoxyphenyl)-3-(3,4-methylenedioxyphenyl) acrylonitrile 3-(3,4-Dimethoxyphenyl)-3-(3,4-methylenedioxyphenyl) acrylonitrile was prepared analogously to methyl 3,3-bis-(3',4'-dimethoxyphenyl)acrylate using 1-(3,4-dimethoxybenzoyl)-3,4-methylenedioxybenzene (1.43 g, 5 mmol), diethylcyanomethylphosphonate (0.91 mL, 5.5 mmol) and lithium hexamethyldisilazide (4.2 mL, 5.5 mmol, 1.3M) with a reaction time of 1 hour at reflux and 24 hours at room temperature. The crude product was purified by chromatography (silica gel, 2% ethyl acetate/methylene chloride) to afford 0.79 g (51%) of a mixture of the E and Z isomers as an off white solid: mp 121–123° C.; $^1$H NMR (CDCl$_3$) δ 7.10–6.73 (m, 12 H), 6.13–5.94 (m, 4 H), 5.57 (s, 1 H), 5.53 (s, 1 H), 3.94 (s, 3 H), 3.92 (s, 3 H), 3.87 (s, 3 H), 3.84 (s, 3 H); $^{13}$C NMR (CDCl$_3$) δ 162.3, 151.0, 150.5, 149.6, 149.1, 148.8, 148.5, 147.9, 133.2, 131.6, 130.8, 129.4, 124.3, 123.5, 123.1, 122.1, 118.5, 118.3, 112.6, 111.1, 110.7, 109.9, 108.5, 108.2, 101.6, 101.5, 92.2, 92.2, 56.0, 55.9, 55.9; Anal. Calcd for $C_{18}H_{15}NO_4$. Theoretical: C, 69.89; H, 4.89; N, 4.53. Found: C, 69.61; H, 5.01; N, 4.37.

EXAMPLE 22

3-(3,4-Dimethoxyphenyl)-3-pyridin-4-ylacrylonitrile (E and Z Isomers)

A. 4-(3,4-Dimethoxybenzoyl)pyridine

A hexane solution of butyl lithium (9 mL, 22 mmol, 2.5M) was slowly added to a stirring solution of 4-bromoveratrole (2.9 mL, 20 mmol) in 40 mL of tetrahydrofuran under nitrogen at −70° C. After 15 minutes a solution of 4-cyanopyridine in 12 mL of tetrahydrofuran was added to the reaction mixture and stirring was continued for 45 minutes. The reaction was then allowed to warm to −10° C. and the reaction was carefully quenched with hydrochloric acid (45 mL, 1N). The mixture was stirred for 30 minutes at room temperature. The pH was then adjusted to 12 with 50 mL of a 10% aqueous solution of sodium hydroxide. The mixture was extracted with ether (3×50 mL). The combined ethereal extracts were washed with brine (100 mL) then dried over magnesium sulfate and concentrated in vacuo to a brown solid. The crude product was purified by flash column chromatography (silica gel, 3% methanol/methylene chloride) to afford after vacuum drying (60° C., 1 mm) 1.9 g (39%) of the product: mp 117–118° C.; $^1$H NMR (CDCl$_3$) δ 8.85–8.76 (m, 2 H), 7.60–7.50 (m, 3 H), 7.40–7.30 (m, 1 H), 6.97–6.88 (m, 1 H), 3.98 (s, 3 H), 3.96 (s, 3 H); $^{13}$C NMR (CDCl$_3$) δ 193.7, 153.9, 150.1, 149.3, 145.2, 128.7, 125.9, 122.6, 111.5, 109.9, 56.1, 56.0; Anal. Calcd for $C_{14}H_{13}NO_3$. Theoretical: C, 69.12; H, 5.39; N, 5.76. Found: C, 69.05; H, 5.39; N, 5.85.

B. 3-(3,4-Dimethoxyphenyl)-3-pyridin-4-ylacrylonitrile 3-(3,4-Dimethoxyphenyl)-3-pyridin-4-ylacrylonitrile was prepared analogously to methyl 3,3-bis-(3',4'-dimethoxyphenyl)acrylate using 4-(3,4-dimethoxybenzoyl) pyridine (1 g, 4 mmol), diethylcyanomethylphosphonate (0.73 mL, 4.4 mmol) and lithium hexamethyldisilazide (3.4 mL, 4.4 mmol, 1.3M) with a reaction time of 24 hours at room temperature. The crude product was slurried in 10 mL of hexane. The mixture was filtered, the solid was washed with hexane, air dried and then dried in vacuo to afford 0.91 g (85%) of a mixture of the E and Z isomers as an off white solid: mp 116–125° C.; $^1$H NMR (CDCl$_3$) δ 8.80–8.63 (m, 4 H), 7.40–7.20 (m, 4 H), 7.04–6.74 (m, 6 H), 5.81 (s, 1 H), 5.70 (s, 1 H), 3.94 (s, 3 H), 3.92 (s, 3 H), 3.87 (s, 3 H), 3.84 (s, 3 H); $^{13}$C NMR (CDCl$_3$) δ 160.1, 157.0, 151.6, 151.1, 150.3, 149.2, 148.9, 146.7, 144.9, 129.6, 127.8, 123.7, 123.1, 122.7, 122.1, 117.4, 117.1, 112.3, 111.0, 110.5, 96.1, 94.8, 56.0, 56.0; Anal. Calcd for $C_{16}H_{14}N_2O_2$. Theoretical: C, 72.17; H, 5.30; N, 10.52. Found: C, 72.35; H, 5.43; N, 10.47.

EXAMPLE 23

3-(3,4-Dimethoxyphenyl)-3-pyridin-2-ylacrylonitrile

A. 2-(3,4-Dimethoxybenzoyl)pyridine 2-(3,4-Dimethoxybenzoyl)pyridine was prepared analogously to 4-(3,4-dimethoxybenzoyl)pyridine using 2-cyanopyridine. The crude mixture was purified by flash column chromatography (silica gel, 1% methanol/methylene chloride) to afford after drying in vacuo (60° C., 1 mm) 1.67 g (34%) of the product: mp 91.5–93° C.; $^1$H NMR (CDCl$_3$) δ 8.76–8.70 (m, 1 H), 8.05–7.71 (m, 4 H), 7.55–7.45 (m, 1 H), 7.00–6.89 (m, 1 H), 3.96 (s, 3 H), 3.96 (s, 3 H); $^{13}$C NMR (CDCl$_3$) δ 192.1, 155.7, 153.3, 148.7, 148.2, 136.9, 128.9, 126.7, 125.7, 124.4, 112.6, 109.8, 56.0, 55.9; Anal. Calcd for $C_{14}H_{13}NO_3$. Theoretical: C, 69.12; H, 5.39; N, 5.76. Found: C, 68.96; H, 5.47; N, 5.66.

B. 3-(3,4-Dimethoxyphenyl)-3-pyridin-2-ylacrylonitrile 3-(3,4-Dimethoxyphenyl)-3-pyridin-2-yl)acrylonitrile was prepared analogously to methyl 3,3-bis-(3',4'- dimethoxyphenyl)acrylate using 2-(3,4-dimethoxybenzoyl) pyridine (1 g, 4 mmol), diethylcyanomethylphosphonate (0.73 mL, 4.4 mmol) and lithium hexamethyldisilazide (3.4 mL, 4.4 mmol, 1.3M) with a reaction time of 17 hours at room temperature. The crude product was purified by flash column chromatography (silica gel, 1% methanol/methylene chloride) to afford 0.8 g (75%) of a mixture of the E and Z isomers as a brown solid. The isomers were separated by additional purification (silica gel, 10% ethyl acetate/methylene chloride) to afford pure samples of each of the isomers.

Isomer 1: mp 125–126° C.; $^1$H NMR (CDCl$_3$) δ 8.75–8.65 (m, 1 H), 7.75–7.60 (m, 1 H), 7.41–7.16 (m, 2 H), 7.10–6.90 (m, 3 H), 6.52 (s, 1 H), 3.95 (s, 3 H), 3.89 (s, 3 H), $^{13}$C NMR (CDCl$_3$) δ 159.9, 154.9, 150.4, 149.9, 148.9, 136.7, 128.0, 124.6, 124.1, 122.6, 118.1, 112.4, 111.1, 97.8, 56.1, 56.0; Anal. Calcd for C$_{16}$H$_{14}$N$_2$O$_2$. Theoretical: C, 72.17; H, 5.30; N, 10.52. Found: C, 71.90; H, 5.28; N, 10.33.

Isomer 2: mp 134.5–135.5° C.; $^1$H NMR (CDCl$_3$) δ 8.82–8.70 (m, 1 H), 7.88–7.76 (m, 1 H), 7.60–7.34 (m, 2 H), 6.94–6.80 (m, 3 H), 5.82 (s, 1 H), 3.91 (s, 3 H), 3.83 (s, 3 H), $^{13}$C NMR (CDCl$_3$) δ 160.8, 155.3, 151.2, 149.9, 149.0, 136.6, 130.2, 124.9, 124.3, 122.1, 117.6, 110.9, 95.4, 56.0; Anal. Calcd for C$_{16}$H$_{14}$N$_2$O$_2$. Theoretical: C, 72.17; H, 5.30; N, 10.52. Found: C, 72.13; H, 5.23; N, 10.40.

EXAMPLE 24

3-(3,4-Dimethoxyphenyl)-3-(2-furyl)acrylonitrile (E and Z Isomers)

A. 2-(3,4-Dimethoxybenzoyl)furane 2-(3,4-Dimethoxybenzoyl)furane was prepared analogously to 3,4,3',4'-tetramethoxybenzophenone using veratrole (1.3 mL, 10 mmol), aluminum chloride (1.5 g, 10 mmol) and 2-furoyl chloride (1.1 mL, 10 mmol) with a reaction time of 2 hours at reflux. The crude product was purified by flash column chromatography (silica gel, 4% ethyl acetate/methylene chloride) to afford 1.69 g (78%) of the product as a white solid: mp 112–114° C.; $^1$H NMR (CDCl$_3$) δ 7.78–7.66 (m, 2 H), 7.59–7.52 (m, 1 H), 7.26–7.17 (m, 1 H), 6.96–6.90 (m, 1 H), 6.63–6.55 (m, 1 H), 3.97 (s, 3 H), 3.96 (s, 3 H); $^{13}$C NMR (CDCl$_3$) δ 180.9, 153.0, 152.5, 148.9, 146.5, 129.8, 124.0, 119.6, 112.0, 111.7, 110.0, 56.0, 55.9; Anal. Calcd for C$_{13}$H$_{12}$O$_4$. Theoretical: C, 67.23; H, 5.21. Found: C, 67.09; H, 5.21.

B. 3-(3,4-Dimethoxyphenyl)-3-(2-furyl)acrylonitrile 3-(3,4-Dimethoxyphenyl)-3-(2-furyl)acrylonitrile was prepared analogously to methyl 3,3-bis-(3',4'-dimethoxyphenyl)acrylate using 2-(3,4-dimethoxybenzoyl)furane (0.87 g, 4 mmol), diethylcyanomethylphosphonate (0.73 mL, 4.4 mmol) and lithium hexamethyldisilazide (3.4 mL, 4.4 mmol, 1.3M) with a reaction time of 3 hours at room temperature. The crude product was purified by chromatography (silica gel, 2% ethyl acetate/methylene chloride) to afford 0.78 g (76%) of a mixture of the E and Z isomers as an off white solid: mp 78–82° C.; $^1$H NMR (CDCl$_3$) δ 7.68–7.73 (m, 2 H), 7.16–6.75 (m, 7 H), 6.54–6.39 (m, 3 H), 5.87 (s, 1 H), 5.30 (s, 1 H), 3.93 (s, 3 H), 3.93 (s, 3 H), 3.91 (s, 3 H), 3.88 (s, 3 H); $^{13}$C NMR (CDCl$_3$) δ 152.0, 150.7, 150.5, 150.4, 149.3, 148.8, 148.7, 148.7, 145.2, 145.0, 129.6, 126.7, 122.1, 121.6, 118.1, 118.0, 116.5, 115.6, 112.5, 112.1, 112.0, 111.5, 110.9, 110.8, 90.5, 90.2, 55.9, 55.9, 55.9, 55.8; Anal. Calcd for C$_{15}$H$_{13}$NO$_3$. Theoretical: C, 70.58; H, 5.13; N, 5.49. Found: C, 70.61; H, 5.09; N, 5.18.

EXAMPLE 25

3-(3,4-Diethylphenyl)-3-phenylacrylonitrile (E and Z Isomers)

A. 3,4-Diethylbenzophenone

To a stirred ice bath cooled solution of diethylbenzene (1.7 mL, 10 mmol) in methylene chloride (30 mL) under nitrogen was added aluminum chloride (2.93 g, 22 mmol). A slight exotherm resulted. To the resulting reaction mixture was added benzoyl chloride (1.2 mL, 10 mmol). The reaction mixture was allowed to warm to room temperature and was then stirred at room temperature for 1.5 hours. The reaction mixture was poured into 60 mL of iced water and stirred for 20 minutes. The resulting mixture was extracted with methylene chloride (2×40 mL). The combined extracts were dried over magnesium sulfate and concentrated in vacuo to afford the crude product as an orange oil. The crude product was purified by flash column chromatography (silica gel, 2.5% ethyl acetate/hexane) to afford 1.22 g (51%) of the product as a yellow oil: $^1$H NMR (CDCl$_3$) δ 7.85–7.41 (m, 7 H), 7.30–7.20 (m, 1 H) 2.83–2.61 (m, 4 H), 1.35–1.17 (m, 6 H); $^{13}$C NMR (CDCl$_3$) δ 196.8, 147.0, 141.9, 138.1, 135.3, 132.1, 132.1, 130.1,130.0, 128.1, 128.1, 25.6, 25.4, 15.1, 15.0; Anal. Calcd for C$_{17}$H$_{18}$O. Theoretical: C, 85.67; H, 7.61. Found: C, 85.38; H, 7.42.

B. 3-(3,4-Diethylphenyl)-3-phenylacrylonitrile 3-(3,4-Diethylphenyl)-3-phenylacrylonitrile was prepared analogously to methyl 3,3-bis-(3,4-dimethoxyphenyl) acrylate using 3,4-diethylbenzophenone (0.95 g, 4 mmol), diethylcyanomethylphosphonate (0.73 mL, 4.4 mmol) and lithium hexamethyldisilazide (3.4 mL, 4.4 mmol, 1.3M) with a reaction time of 2 hours at room temperature. The crude product was purified by flash chromatography (silica gel, 8% ethyl acetate/methylene chloride) to afford an oil which was stirred in hexane until it solidified. The resulting slurry was filtered, the solid washed with hexane, air dried and then dried in vacuo to afford 0.6 g (57%) of a mixture of the E and Z isomers as a white solid: mp 63–64° C.; $^1$H NMR (CDCl$_3$) δ 7.51–6.99 (m, 16 H), 5.72 (s, 2 H), 2.76–2.55 (m, 8 H), 1.32–1.14 (m, 12 H); $^{13}$C NMR (CDCl$_3$) δ 163.3, 144.7, 142.2, 137.3, 136.5, 130.2, 129.8, 129.6, 128.6, 128.5, 128.4, 128.3, 127.2, 126.2, 118.2, 93.9, 93.7, 25.5, 25.3, 15.2, 15.0.

EXAMPLE 26

3-(3,4-Diethylphenyl)-3-(3,4-dimethoxyphenyl) acrylonitrile

A. 3',4'-Diethyl-3,4-dimethoxybenzophenone

3',4'-Diethyl-3,4-dimethoxybenzophenone was prepared analogously to 3,4-diethylbenzophenone using diethylbenzene (2.5 mL, 15 mmol), aluminum chloride (2.2 g, 16.5 mmol) and 3,4-dimethoxybenzoyl chloride (3 g, 15 mmol) with a reaction time of 3 hours at reflux. The crude product was purified by flash column chromatography (silica gel, 1.5% ethyl acetate/hexane) to afford 0.84 g (20%) of the product as an orange solid: mp 60–61° C.; $^1$H NMR (CDCl$_3$) δ 7.74–7.15 (m, 5 H), 7.00–6.80 (m, 1 H) 3.96 (s, 3 H), 3.94 (s, 3 H), 2.93–2.60 (m, 4 H), 1.43–1.15 (m, 6 H); $^{13}$C NMR (CDCl$_3$) δ 195.5, 152.7, 148.8, 146.3, 141.7, 135.9, 130.6, 129.8, 128.0, 127.7, 125.1, 112.2, 109.7, 56.0, 25.6, 25.4, 15.1, 15.0; Anal. Calcd for C$_{19}$H$_{22}$O$_3$. Theoretical: C, 76.48; H, 7.43. Found: C, 76.53; H, 7.34.

B. 3-(3,4-Diethylphenyl)-3-(3,4-dimethoxyphenyl) acrylonitrile 3-(3,4-Diethylphenyl)-3-(3,4-dimethoxyphenyl) acrylonitrile was prepared analogously to methyl 3,3-bis-(3,4-dimethoxyphenyl)acrylate using 3',4'-diethyl-3,4- dimethoxybenzophenone (0.51 g, 1.7 mmol), diethylcyanomethylphosphonate (0.31 mL, 1.9 mmol) and lithium hexamethyldisilazide (1.4 mL, 1.9 mmol, 1.3M) with a reaction time of 60 hours at room temperature. The crude product was purified by chromatography (silica gel, 1% ethyl acetate/methylene chloride) to afford an oil which was stirred in hexane until it solidified. The resulting slurry was filtered, the solid washed with hexane, air dried, and dried in vacuo to afford 0.31 g (57%) of a mixture of the E and Z isomers as an off white solid: mp 78–82° C.; $^1$H NMR (CDCl$_3$) δ 7.30–6.75 (m, 12 H), 5.61 (s, 1 H), 5.60 (s, 1 H), 3.94 (s, 3 H), 3.92 (s, 3 H), 3.87 (s, 3 H), 3.83 (s, 3 H), 2.80–2.59 (m, 8 H), 1.35–1.14 (m, 12 H); $^{13}$C NMR (CDCl$_3$) δ 163.0, 163.0, 151.0, 150.5, 148.8, 148.6, 144.6, 143.9, 142.1, 141.8, 136.8, 134.5, 131.9, 129.7, 128.6, 128.5, 128.2, 127.3, 126.3, 123.2, 122.2, 118.7, 118.6, 112.8, 111.3, 110.7, 92.5, 92.2, 56.1, 56.0, 25.5, 25.4, 25.4, 25.3, 15.3, 15.2, 15.0, 14.9; Anal. Calcd for C$_{21}$H$_{23}$NO$_2$. Theoretical: C, 78.47; H, 7.21; N, 4.36. Found: C, 77.80; H, 7.25; N, 4.68.

EXAMPLE 27

4-(3-Ethoxy-4-methoxyphenyl)-4-phenyl-3-butan-2-one

To a suspension of cuprous cyanide (0.21 g, 2.3 mmol) in tetrahydrofuran (8 mL) at −70° C. under nitrogen was added a cyclohexyl/ether solution of phenyl lithium (2.6 mL, 4.6 mmol, 1.8M). After 45 minutes a solution of 4-(3-ethoxy-4-methoxyphenyl)-3-buten-2-one (0.51 g, 2,3 mmol) in 10 mL of tetrahydrofiran was slowly added to the reaction mixture. After 1 hour at −78° C. the mixture was allowed to warm to room temperature. The reaction mixture was then carefully quenched with 10 mL of an aqueous solution of ammonium chloride. The resulting mixture was extracted with methylene chloride (3×10 mL). The combined organic extracts were dried over magnesium sulfate and concentrated in vacuo to afford 0.7 g of the crude product. The crude product was purified by chromatography (silica gel, 2% ethyl acetate/methylene chloride) to afford 0.41 g (60%) of the product as an oil which solidified: mp 57–58° C.; $^1$H NMR (CDCl$_3$) δ 7.31–7.13 (m, 5 H), 6.83–6.69 (m, 3 H), 4.48 (t, J=7.5 Hz, 1 H), 4.03 (q, J=7 Hz, 2 H), 3.82 (s, 3 H), 3.13 (d, J=7.5 Hz, 2 H), 2.07 (s, 3 H), 1.41 (t, J=7 Hz, 3 H); $^{13}$C NMR (CDCl$_3$) δ 207.0, 148.2, 148.0, 144.2, 136.4, 128.6, 127.6, 126.4, 119.4, 113.0, 111.5, 64.3, 55.9, 49.9, 45.6, 30.6, 14.8; Anal. Calcd for C$_{19}$H$_{22}$O$_3$. Theoretical: C, 76.48; H, 7.43. Found: C, 76.81; H, 7.44.

EXAMPLE 28

3-(3,4-Dimethoxyphenyl)-3-(naphth-1-yl) acrylonitrile 1-(3,4-Dimethoxybenzoyl)naphthalene was prepared analogously to 3,4,3',4'-tetramethoxybenzophenone using veratrole (1.3 mL, 10 mmol), aluminum chloride (1.5 g, 11 mmol) and 1-naphthoyl chloride (1.5 mL, 10 mmol) with a reaction time of 24 hours at room temperature. The crude product was purified by flash column chromatography (silica gel, 2.5% ethyl acetate/methylene chloride) to afford 1.85 g (63%) of the product as a white solid: mp 92.5–94.5° C.; $^1$H NMR (CDCl$_3$) δ 8.06–7.84 (m, 3 H), 7.80–7.39 (m, 5 H), 7.31–7.21 (m, 1 H), 6.84–6.74 (m, 1 H), 3.94 (s, 3 H), 3.91 (s, 3 H); $^{13}$C NMR (CDCl$_3$) δ 196.6, 153.5, 149.0, 136.8, 133.6, 131.1, 130.9, 130.5, 128.2, 126.9, 126.7, 126.3, 126.3, 125.6, 124.3, 111.3, 109.7, 56.0, 55.9; Anal. Calcd for C$_{19}$H$_{16}$O$_3$. Theoretical: C, 78.06; H, 5.52. Found: C, 77.97; H, 5.66.

3-(3,4-Dimethoxyphenyl)-3-(naphth-1-yl)acrylonitrile is prepared in a fashion similar to that described in Example 20.

EXAMPLE 29

3-(3,4-Dimethoxyphenyl)-3-(2,5-dichlorophenyl) acrylonitrile

2',5'-Dichloro-3,4-dimethoxybenzophenone was prepared analogously to 3,4,3',4'-tetramethoxybenzophenone using veratrole (2.15 mL, 15 mmol), aluminum chloride (2.2 g, 16.5 mmol) and 2,5-dichlorobenzoyl chloride (1.9 mL, 15 mmol) with a reaction time of 3 hours at reflux. The crude product was purified by flash column chromatography (silica gel, 2.5% ethyl acetate/methylene chloride) to afford 3.88 g (83%) of the product as a white solid: mp 129–130° C.; $^1$H NMR (CDCl$_3$) δ 7.65–7.56 (m, 1 H), 7.41–7.12 (m, 4 H), 6.89–6.81 (m, 1 H), 3.96 (s, 3 H), 3.94 (s, 3 H); $^{13}$C NMR (CDCl$_3$) δ 191.1, 154.4 149.6, 137.9, 132.0, 130.5, 128.7, 128.0, 125.7, 110.2, 56.1, 56.0; Anal. Calcd for C$_{15}$H$_{12}$Cl$_2$O$_3$. Theoretical: C, 57.90; H, 3.89. Found: C, 57.58; H, 3.87.

3-(3,4-Dimethoxyphenyl)-3-(2,5-dichlorophenyl) acrylonitrile is prepared in an analogous fashion as described in Example 26 starting with 5'-dichloro-3,4-dimethoxybenzophenone.

EXAMPLE 30

2',6',3,4-Tetramethoxybenzophenone

2',6',3,4-Tetramethoxybenzophenone was prepared analogously to 3,4,3',4'-tetramethoxybenzophenone except using veratrole (1.3 mL, 10 mmol), aluminum chloride (1.47 g, 11 mmol) and 2,6-dimethoxybenzoyl chloride (2.0 mL, 10 mmol) with a reaction time of 24 hours at room temperature. The crude reaction mixture was purified by flash column chromatography (silica gel, 4% ethyl acetate/methylene chloride) to afford 2.11 g (70%) of the product as a white solid: mp 128–129° C.; $^1$H NMR (CDCl$_3$) δ 7.66–7.60 (m, 1 H), 7.40–7.20 (m, 2 H), 6.88–6.79 (m, 1 H), 6.67–6.65 (m, 2 H), 3.93 (s, 3 H), 3.91 (s, 3 H), 3.71 (s, 6 H); $^{13}$C NMR (CDCl$_3$) δ 193.8, 157.4, 153.4, 148.9, 130.9, 130.5, 125.3, 118.0, 110.2, 109.9, 104.0, 55.9, 55.8; Anal. Calcd for C$_{17}$H$_{18}$O$_5$. Theoretical: C, 67.54; H, 6.00. Found: C, 66.51; H, 5.91.

3-(3,4-Dimethoxyphenyl)-3-(2,6-dimethoxyphenyl) acrylonitrile is prepared in an analogous fashion as described in Example 10 starting with 2',6',3,4-tetramethoxybenzophenone.

EXAMPLE 31

Tablets, each containing 50 milligrams of active ingredient, can be prepared in the following manner:

| Constituents (for 1000 tablets) | |
| --- | --- |
| active ingredient | 50.0 grams |
| lactose | 50.7 grams |
| wheat starch | 7.5 grams |
| polyethylene glycol 6000 | 5.0 grams |
| talc | 5.0 grams |
| magnesium stearate | 1.8 grams |
| demineralized water | q.s. |

The solid ingredients are first forced through a sieve of 0.6 mm mesh width. The active ingredient, the lactose, the talc, the magnesium stearate and half of the starch then are mixed. The other half of the starch is suspended in 40 milliliters of water and this suspension is added to a boiling solution of the polyethylene glycol in 100 milliliters of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 32

Tablets, each containing 100 milligrams of active ingredient, can be prepared in the following manner:

| Constituents (for 1000 tablets) | |
| --- | --- |
| active ingredient | 100.0 grams |
| lactose | 100.0 grams |
| wheat starch | 47.0 grams |
| magnesium stearate | 3.0 grams |

All the solid ingredients are first forced through a sieve of 0.6 mm mesh width. The active ingredient, the lactose, the magnesium stearate and half of the starch then are mixed. The other half of the starch is suspended in 40 milliliters of water and this suspension is added to 100 milliliters of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 33

Tablets for chewing, each containing 75 milligrams of active ingredient, can be prepared in the following manner:

| Composition (for 1000 tablets) | |
| --- | --- |
| active ingredient | 75.0 grams |
| mannitol | 230.0 grams |
| lactose | 150.0 grams |
| talc | 21.0 grams |
| glycine | 12.5 grams |
| stearic acid | 10.0 grams |
| saccharin | 1.5 grams |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. The active ingredient, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 34

Tablets, each containing 10 milligrams of active ingredient, can be prepared in the following manner:

| Composition (for 1000 tablets) | |
| --- | --- |
| active ingredient | 10.0 grams |
| lactose | 328.5 grams |
| corn starch | 17.5 grams |
| polyethylene glycol 6000 | 5.0 grams |
| talc | 25.0 grams |
| magnesium stearate | 4.0 grams |
| demineralized water | q.s. |

The solid ingredients are first forced through a sieve of 0.6 mm mesh width. Then the active ingredient, lactose, talc, magnesium stearate and half of the starch are intimately mixed. The other half of the starch is suspended in 65 milliliters of water and this suspension is added to a boiling solution of the polyethylene glycol in 260 milliliters of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 35

Gelatin dry-filled capsules, each containing 100 milligrams of active ingredient, can be prepared in the following manner:

| Composition (for 1000 capsules) | |
| --- | --- |
| active ingredient | 100.0 grams |
| microcrystalline cellulose | 30.0 grams |
| sodium lauryl sulphate | 2.0 grams |
| magnesium stearate | 8.0 grams |

The sodium lauryl sulphate is sieved into the active ingredient through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 milligrams each into size 0 (elongated) gelatin dry-fill capsules.

EXAMPLE 36

A 0.2% injection or infusion solution can be prepared, for example, in the following manner:

| | |
| --- | --- |
| active ingredient | 5.0 grams |
| sodium chloride | 22.5 grams |
| phosphate buffer pH 7.4 | 300.0 grams |
| demineralized water to 2500.0 milliliters | |

The active ingredient is dissolved in 1000 milliliters of water and filtered through a microfilter or slurried in 1000 mL of $H_2O$. The buffer solution is added and the whole is made up to 2500 milliliters with water. To prepare dosage unit forms, portions of 1.0 or 2.5 milliliters each are introduced into glass ampoules (each containing respectively 2.0 or 5.0 milligrams of active ingredient).

What is claimed is:

1. A compound of the formula:

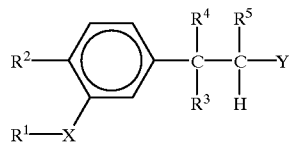

in which:
(a) X is —O— or —$(C_nH_{2n})$— in which n has a value of 0, 1, 2, or 3, and $R^1$ is alkyl of one to 10 carbon atoms, monocycloalkyl of up to 10 carbon atoms, polycycloalkyl of up to 10 carbon atoms, or benzocyclic alkyl of up to 10 carbon atoms, or
(b) X is —CH═ and $R^1$ is alkylidene of up to 10 carbon atoms, monocycloalkylidene of up to 10 carbon atoms, or bicycloalkylidene of up to 10 carbon atoms;

$R^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;

$R^3$ is pyridyl, unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, or phenyl;

each of $R^4$ and $R^5$ taken individually is hydrogen or $R^4$ and $R^5$ taken together are a carbon-carbon bond;

Y is —COZ, —C≡N, or lower alkyl of 1 to 5 carbon atoms;

Z is —OH, —$NR^6R^6$, —$R^7$, or —$OR^7$;

$R^6$ is hydrogen or lower alkyl; and $R^7$ is alkyl or benzyl.

2. A compound according to claim 1 in which $R^1$ is alkyl, monocycloalkyl of up to 10 carbon atoms, polycycloalkyl of up to 10 carbon atoms, or benzocyclic alkyl of up to 10 carbon atoms; X is —$(CH_2)_n$— or —O—, where n=0, 1, 2, or 3; $R^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkoxy, halo; and $R^4$, $R^5$, Y, Z, $R^6$, and $R^7$ are as therein defined.

3. A compound according to claim 1 in which:
X is —O—;
$R^1$ is alkyl of one to 10 carbon atoms, monocycloalkyl of up to 10 carbon atoms, polycycloalkyl of up to 10 carbon atoms, or benzocyclic alkyl of up to 10 carbon atoms;
$R^2$ is hydrogen, nitro, cyano, trifluoromethyl, carbethoxy, carbomethoxy, carbopropoxy, acetyl, carbamoyl, acetoxy, carboxy, hydroxy, amino, lower alkyl, lower alkylidenemethyl, lower alkoxy, or halo;
$R^3$ is pyridyl, unsubstituted or substituted with 1 or more substituents each selected independently from the group consisting of nitro, cyano, halo, trifluoromethyl, carbethoxy, carbomethoxy, carbopropoxy, acetyl, carbamoyl, acetoxy, carboxy, hydroxy, amino, substituted amino, alkyl of 1 to 10 carbon atoms, alkoxy of 1 to 10 carbon atoms, phenyl;

each of $R^4$ and $R^5$ taken individually is hydrogen or $R^4$ and $R^1$ taken together are a carbon-carbon bond;

Y is —COZ, —C≡N, or lower alkyl of 1 to 5 carbon atoms;

Z is —OH, —$NR^6R^6$, —$R^7$, or —$OR^7$;

$R^6$ is hydrogen or lower alkyl; and $R^7$ is alkyl or benzyl.

4. A compound according to claim 3, wherein $R^3$ is 2-pyridyl; 3-pyridyl; or 4-pyridyl, each $R^4$ and $R^5$ is hydrogen, and Y is —COZ in which Z is as therein defined.

5. A compound according to claim 3, wherein $R^3$ is 2-pyridyl; 3-pyridyl; or 4-pyridyl, $R^4$ and $R^5$ together are a carbon-carbon bond;, and Y is —COZ in which Z is as therein defined.

6. A compound according to claim 3, which is 4-(3-ethoxy-4-methoxyphenyl)-4-(4-pyridyl)but-3-en-2-one; 4-(3-ethoxy-4-methoxyphenyl)-4-(4-pyridyl)butan-2-one; 4-(3-cyclopentoxy-4-methoxyphenyl)-4-(4-pyridyl)but-3-en-2-one; 4-(3-cyclopentoxy-4-methoxyphenyl)-4-(4-pyridyl)butan-2-one; methyl 3-(3-cyclopentoxy-4-methoxyphenyl)-3-(4-pyridyl)prop-2-enoate; methyl 3-(3-ethoxy-4-methoxyphenyl)-3-(4-pyridyl)prop-2-enoate; methyl 3-(3-ethoxy-4-methoxyphenyl)-3-(4-pyridyl)propanoate; 3-(3-ethoxy-4-methoxyphenyl)-3-(4-pyridyl)prop-2-enenitrile; 3-(3-ethoxy-4-methoxyphenyl)-3-(4-pyridyl)propanenitrile; 3-(3-cyclopentoxy-4-methoxyphenyl)-3-(4-pyridyl)prop-2-enenitrile; or 3-(3-cyclopentoxy-4-methoxyphenyl)-3-(4-pyridyl)propanenitrile.

7. A method which comprises administering to a mammal an amount of a compound according to claim 1 which amount is effective to inhibit at least one of the enzymatic actions of phosphodiesterase, the level of $TNF_\alpha$ and translocation of NFκB to the nucleus which comprises reducing the levels of phosphodiesterases, $TNF_\alpha$ and NFκB in mammals by administering thereto an effective amount of a compound according to claim 1.

8. A pharmaceutical composition comprising a compound according to claim 1 in an amount effective upon single or multiple dosage to inhibit at least one of the enzymatic actions of phosphodiesterase, the level of $TNF_\alpha$ and translocation of NFκB to the nucleus, in combination with a pharmaceutical carrier.

9. A method which comprises administering to a mammal an amount of a compound according to claim 3 which amount is effective to inhibit at least one of the enzymatic action of phosphodiesterase, the level of $TNF_\alpha$ and translocation of NFκB to the nucleus which comprises reducing the levels of phosphodiesterases, $TNF_\alpha$ and NFκB in mammals by administering thereto an effective amount of a compound according to claim 3.

10. A pharmaceutical composition comprising a compound according to claim 3 in an amount effective upon single or multiple dosage to inhibit at least one of the enzymatic action of phosphodiesterase, the level of $TNF_\alpha$ and translocation of NFκB to the nucleus, in combination with a pharmaceutical carrier.

* * * * *